(12) United States Patent
Saint et al.

(10) Patent No.: US 11,568,975 B2
(45) Date of Patent: Jan. 31, 2023

(54) INTELLIGENT MEDICATION DELIVERY SYSTEMS AND METHODS FOR DOSE RECOMMENDATION AND MANAGEMENT

(71) Applicant: MEDTRONIC MINIMED, INC., Northridge, CA (US)

(72) Inventors: Sean Saint, San Diego, CA (US); Jack Pryor, Ladera Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 129 days.

(21) Appl. No.: 16/754,555

(22) PCT Filed: Oct. 12, 2018

(86) PCT No.: PCT/US2018/055646
§ 371 (c)(1),
(2) Date: Apr. 8, 2020

(87) PCT Pub. No.: WO2019/075352
PCT Pub. Date: Apr. 18, 2019

(65) Prior Publication Data
US 2020/0350052 A1 Nov. 5, 2020

Related U.S. Application Data

(60) Provisional application No. 62/571,538, filed on Oct. 12, 2017.

(51) Int. Cl.
*G16H 20/17* (2018.01)
*G16H 20/30* (2018.01)
(Continued)

(52) U.S. Cl.
CPC ............. *G16H 20/17* (2018.01); *A61K 38/28* (2013.01); *A61M 5/31546* (2013.01);
(Continued)

(58) Field of Classification Search
CPC ........ G16H 10/40; G16H 20/17; G16H 20/30; G16H 40/67
(Continued)

(56) References Cited

U.S. PATENT DOCUMENTS 4,498,904 A 2/1985 Turner et al.
4,515,584 A 5/1985 Abe et al.
(Continued)

FOREIGN PATENT DOCUMENTS

EP 0298067 A1 4/1989
EP 513128 A1 11/1992
(Continued)

OTHER PUBLICATIONS

Ahmadalinezhad, Asieh; Nanomaterial-based Electrochemical Sensors for the Detection of Glucose and Cholesterol; Lakehead University (Canada). ProQuest Dissertations Publishing, 2011. NR78489. (Year: 2011).*
(Continued)

*Primary Examiner* — Hiep V Nguyen
(74) *Attorney, Agent, or Firm* — Carter, DeLuca & Farrell LLP

(57) ABSTRACT

Systems, devices, and techniques are disclosed for administering and tracking medicine to patients and providing health management capabilities for patients and caregivers. In some aspects, a method includes receiving one or more analyte values associated with a health condition of the patient user; receiving contextual data associated with the patient user obtained by the mobile computing device, where the obtained contextual data includes information associated with a meal; determining a medicine metric value associated with an amount of medicine active in the body of the patient user; autonomously calculating a dose of the medicine without input from the user based at least on the
(Continued)

one or more analyte values, the medicine metric value, and the information associated with a meal; and continuously displaying the calculated dose of the medicine.

26 Claims, 15 Drawing Sheets

(51) Int. Cl.
  *G16H 40/67* (2018.01)
  *G16H 10/40* (2018.01)
  *G16H 10/60* (2018.01)
  *G16H 50/70* (2018.01)
  *G16H 50/20* (2018.01)
  *G16H 70/40* (2018.01)
  *G16H 20/60* (2018.01)
  *A61K 38/28* (2006.01)
  *A61M 5/315* (2006.01)

(52) U.S. Cl.
  CPC ............ *G16H 10/40* (2018.01); *G16H 10/60* (2018.01); *G16H 20/30* (2018.01); *G16H 20/60* (2018.01); *G16H 40/67* (2018.01); *G16H 50/20* (2018.01); *G16H 50/70* (2018.01); *G16H 70/40* (2018.01); *A61M 2205/18* (2013.01); *A61M 2205/3584* (2013.01); *A61M 2205/3592* (2013.01); *A61M 2205/52* (2013.01); *A61M 2205/581* (2013.01); *A61M 2205/582* (2013.01); *A61M 2205/583* (2013.01); *A61M 2230/06* (2013.01); *A61M 2230/201* (2013.01); *A61M 2230/30* (2013.01)

(58) Field of Classification Search
  USPC .......................................................... 705/2
  See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,591,801 B2 | 9/2009 | Brauker et al. |
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |

(56) References Cited

U.S. PATENT DOCUMENTS

| | | |
|---|---|---|
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0280329 A1 | 11/2010 | Randlov et al. |
| 2010/0331656 A1 | 12/2010 | Mensinger et al. |
| 2010/0331657 A1* | 12/2010 | Mensinger ............ G16H 40/63 340/870.07 |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0257065 A1 | 9/2014 | Walsh |
| 2014/0276531 A1 | 9/2014 | Walsh |
| 2014/0288494 A1 | 9/2014 | Brister et al. |
| 2015/0073337 A1 | 3/2015 | Saint et al. |
| 2015/0126963 A1* | 5/2015 | Despa ................. G16H 40/63 604/506 |
| 2015/0202377 A1 | 7/2015 | Haupt |
| 2015/0351683 A1 | 12/2015 | Brauker et al. |
| 2015/0359965 A1 | 12/2015 | O'Connor et al. |
| 2016/0012205 A1* | 1/2016 | Saint ................... H04B 7/24 604/154 |
| 2016/0030683 A1 | 2/2016 | Taylor |
| 2016/0063734 A1 | 3/2016 | Divakaran et al. |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju et al. |
| 2017/0189625 A1 | 7/2017 | Cirillo et al. |
| 2017/0216518 A1 | 8/2017 | Davis et al. |
| 2017/0270276 A1* | 9/2017 | Saint ................... G16H 40/63 |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0015596 A1 | 1/2019 | Saint et al. |
| 2019/0035500 A1 | 1/2019 | Saint et al. |
| 2019/0132801 A1 | 5/2019 | Kamath et al. |
| 2019/0173885 A1 | 6/2019 | Kamath et al. |
| 2019/0125224 A1 | 8/2019 | Kamath et al. |

FOREIGN PATENT DOCUMENTS

| | | | |
|---|---|---|---|
| EP | 927057 A1 | 7/1999 | |
| EP | 2572740 A1 | 3/2013 | |
| WO | 9638190 A1 | 12/1996 | |
| WO | 2007069118 A2 | 6/2007 | |
| WO | 2010052275 A2 | 5/2010 | |
| WO | 2011041007 A1 | 4/2011 | |
| WO | 2012046199 A1 | 4/2012 | |
| WO | 2013053695 A1 | 4/2013 | |
| WO | 2014128157 A1 | 8/2014 | |
| WO | 2015047870 A1 | 4/2015 | |
| WO | 2015169814 A1 | 11/2015 | |
| WO | 2015185686 A1 | 12/2015 | |
| WO | WO-2016007935 A2 * | 1/2016 | ........ A61M 5/31528 |
| WO | WO-2016011207 A1 * | 1/2016 | ................ A61J 1/16 |
| WO | 2016019192 A1 | 2/2016 | |
| WO | 2016071912 A1 | 5/2016 | |
| WO | 2017132577 A1 | 3/2018 | |

OTHER PUBLICATIONS

Extended European Search Report issued in corresponding European Application No. EP 18865823.1 dated Jul. 2, 2021, 11 pages.
Cision PR News Wire, "CompaNion Medical Announces Insights by InPen, the Future of MDI Reports", Jun. 20, 2018.
EPO, Extended European Search Report for European Patent Application No. 14849422.2, dated May 4, 2017, 11 pages.
EPO, Extended European Search Report for European Patent Application No. 17745019.4, dated Aug. 6, 2019, 9 pages.
ISA, International Search Report and Written Opinion for PCT Application No. PCT/US2014/056336, dated Dec. 31, 2014, 10 pages.
ISA, International Search Report and Written Opinion for PCT Application No. PCT/US2018/55646, dated Feb. 6, 2019, 15 pages.
ISA, International Search Report and Written Opinion for PCT Application No. PCT/US2017/15452, dated May 23, 2017, 14 pages.
ISA, International Search Report and Written Opinion for PCT Application No. PCT/US2018/036768; dated Aug. 31, 2018, 10 pages.
ISA, Invitation to Pay Additional Fees and Partial Search Report for PCT Application No. PCT/US15/40069, dated Oct. 1, 2015, 2 pages.
ISA, International Search Report for PCT Application No. PCT/US15/40069, dated Dec. 22, 2015, 13 pages.

* cited by examiner

Streamlined Dose Calculator
(Requiring no manual input by user)

Example User Interfaces

IOB: 2.5 u
Glucose: 155 mg/dL

Current Recommendation
with No Meal:
1.0 units of Insulin

IOB: 2.5 u
Glucose: 155 mg/dL

Current Recommendation
with a Regular Meal:
2.0 units of Insulin

IOB: 2.5 u
Glucose: 155 mg/dL

Current Recommendations
of Insulin:
• No Food: 1.0 units
• Small Meal: 2.0 units
• Medium Meal: 3.5 units
• Large Meal: 5.0 units

FIG. 3C

*Single setpoint for meals*

*Setpoints for meal types*

*Setpoints for meal sizes*

*Setpoints for meal types & sizes*

*Single Setpoint for Meals*

| Meal Size |
|---|
| 15 Carbs |

FIG. 6A

*Setpoint for Meal Types*

| Meal Sizes |
|---|
| Breakfast |
| 8 Carbs |
| Lunch |
| 12 Carbs |
| Dinner |
| 20 Carbs |

FIG. 6B

*Setpoint for Meal Sizes*

| Meal Sizes |
|---|
| Small |
| 8 Carbs |
| Medium |
| 12 Carbs |
| Large |
| 20 Carbs |

FIG. 6C

*Setpoint for Meal Types and Sizes*

| Meal Sizes | | | |
|---|---|---|---|
| Grams of Carbohydrate | | | |
| | Small | Med | Large |
| Breakfast | 2 | 2 | 2 |
| Lunch | 3.5 | 3.5 | 3.5 |
| Dinner | 6 | 6 | 6 |

FIG. 6D

*Range of small to large defined by settings*
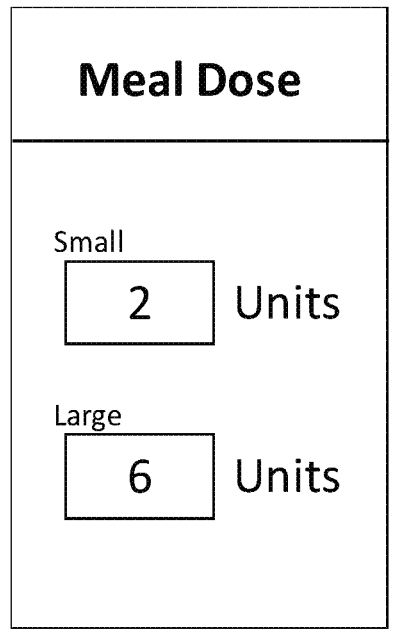
FIG. 7A
*User drags slider to estimate meal size*
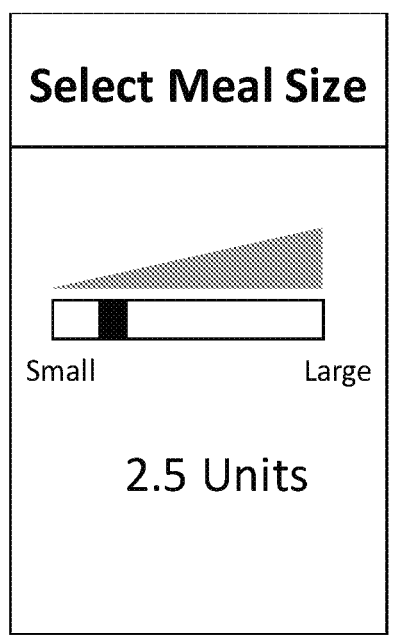 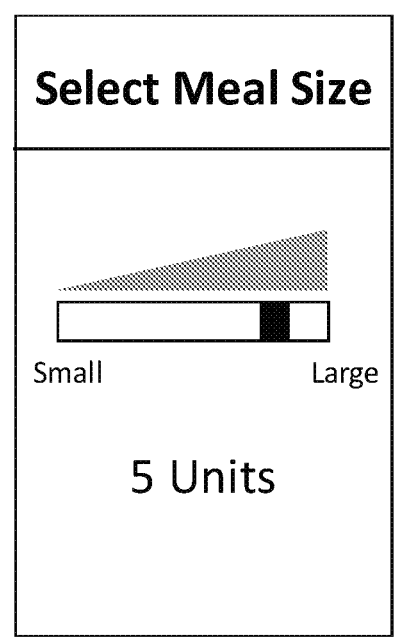
FIG. 7B    FIG. 7C

*Range of small to large defined by settings*
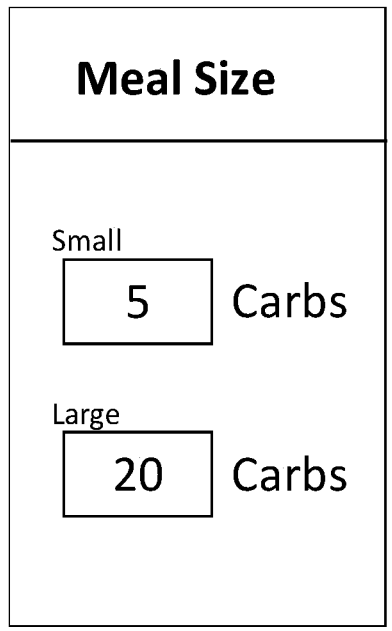
FIG. 8A
*User drags slider to estimate meal size*
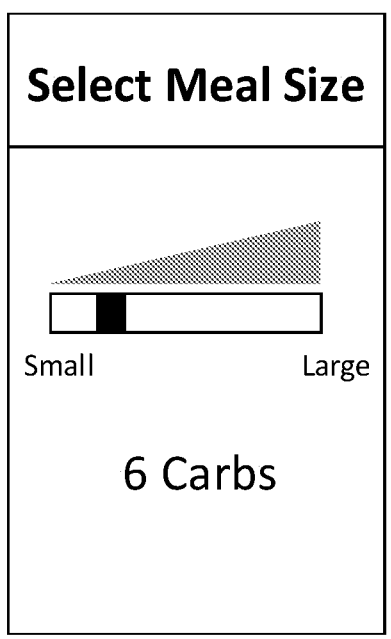 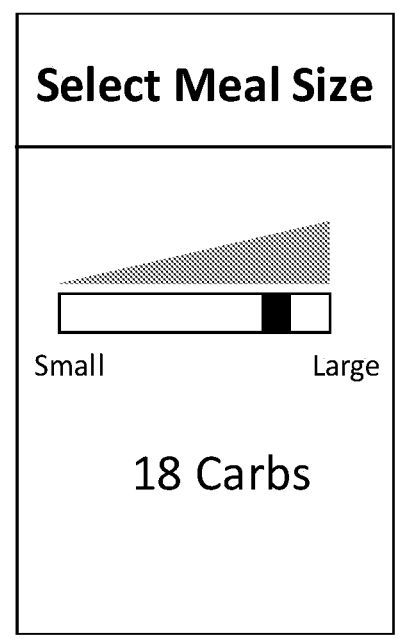
FIG. 8B  FIG. 8C

FIG. 11

INTELLIGENT MEDICATION DELIVERY SYSTEMS AND METHODS FOR DOSE RECOMMENDATION AND MANAGEMENT

CROSS-REFERENCE TO RELATED APPLICATIONS

This patent document is a 371 National Phase Application of PCT Application No. PCT/US2018/055646 entitled "INTELLIGENT MEDICATION DELIVERY SYSTEMS AND METHODS FOR DOSE RECOMMENDATION AND MANAGEMENT" filed on Oct. 12, 2018 which claims priorities to and benefits of U.S. Provisional Patent Application No. 62/571,538 entitled "INTELLIGENT MEDICATION DELIVERY SYSTEMS AND METHODS FOR DOSE RECOMMENDATION AND MANAGEMENT" filed on Oct. 12, 2017. The entire content of the aforementioned patent application is incorporated by reference as part of the disclosure of this patent document.

TECHNICAL FIELD

This patent document relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering and tracking medicine to patients and providing health management capabilities for patients and caregivers.

In some aspects, a system for administering a medicine includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data, the injection pen device in wireless communication with a mobile communication device including a data processing unit including a processor and memory to receive and process the dose data, in which the mobile communication device includes a software application program product comprising a non-transitory computer-readable storage medium having instructions, which when executed by the processor of the data processing unit, cause the mobile communication device to determine a recommended dose based on health data and contextual data associated with a user of the injection pen device, the health data including one or more analyte values associated with a health condition, and the contextual data including one or more of physical activity data, location data, or nutrient data corresponding to a food, in which the software application program product includes (i) a data aggregator that obtains the health data and the contextual data, (ii) a dose calculator that autonomously determines the recommended dose of the medicine, and (iii) a user interface generator to produce a user interface on a display of the mobile communication device that persistently displays, on the produced user interface, the recommended dose.

In some aspects, a method for determining a medicine dose for administering to a patient user by an injection pen device includes receiving, by a software application operable on a mobile computing device of the patient user, one or more analyte values associated with a health condition of the patient user; receiving, by the software application, contextual data associated with the patient user obtained by the mobile computing device, in which the obtained contextual data includes information associated with a meal including at least one of an amount of carbohydrates or calories associated with the meal; determining, by the software application, a medicine metric value associated with an amount of medicine active in the body of the patient user; autonomously calculating a dose of the medicine without input from the user based at least on the one or more analyte values, the medicine metric value, and the information associated with a meal; and continuously displaying, on a display of the mobile computing device or an injection pen device in communication with the mobile computing device, the calculated dose of the medicine.

In some aspects, a method for autonomously adjusting a predetermined fixed insulin dose, includes receiving, by a software application operable on a mobile computing device of a patient user, one or more glucose values associated with a health condition of the patient user; determining, by the software application, an insulin metric value associated with the patient user based on insulin on board (IOB) data pertaining to an estimated amount of insulin medicine active in the body of the patient user; autonomously calculating, by the software application, a dose of the insulin medicine without input from the user based at least on the one or more glucose values and the insulin metric value, in which the autonomously calculating the dose of the insulin medicine includes determining a first dose of a sequence of titration doses of the insulin medicine according to a titration protocol to cause a current glucose level of the patient user to lower a target glucose level; displaying, on a display of the mobile computing device or a device in communication with the mobile computing device, the calculated dose of the insulin medicine; and monitoring a response to administration of the first dose, including: (a) receiving an updated glucose value corresponding to the current glucose level, (b) determining whether the updated glucose value is within a range associated with the target glucose level, (c) when it is determined that the updated glucose value is above the range after one or more meals, re-calculating a second dose according to the titration protocol, and displaying the second dose on the display device, and (d) repeating (a), (b), (c) until the current glucose level reaches the target glucose level acceptable within a predetermined time frame.

BRIEF DESCRIPTION OF THE DRAWINGS

FIG. 3C shows an example diagram illustrating an example user interface for continuous display of a recommended dose of insulin medicine in an 'always available' implementation of a streamline dose calculator module in accordance with certain embodiments of the present technology.

FIGS. 6A-6D show diagrams of an example user interface of a software application on a companion device for a single fixed meal size estimation and for fixed meal sizes based on meal type, meal size, or a combination thereof.

FIG. 7A shows a diagram of an example interface of a software application on a companion device for setting meal dose range based on meal size.

FIGS. 7B and 7C show diagrams depicting example user interfaces of a software application on a companion device for selecting meal dose on a sliding scale of meal size, with a smaller meal size selected and with a meal larger size selected, respectively.

FIG. 8A shows a diagram of an example interface of a software application on a companion device for setting meal carb estimation range based on meal size.

FIGS. 8B and 8C show diagrams depicting example user interfaces of a software application on a companion device for selecting meal carb estimation on a sliding scale of meal size, with a smaller meal size selected and with a meal larger size selected, respectively.

FIG. 11 shows an illustration depicting a physician app for entering user settings, with the settings electronically transferred to a software application on a companion device.

DETAILED DESCRIPTION

Figure 1A:
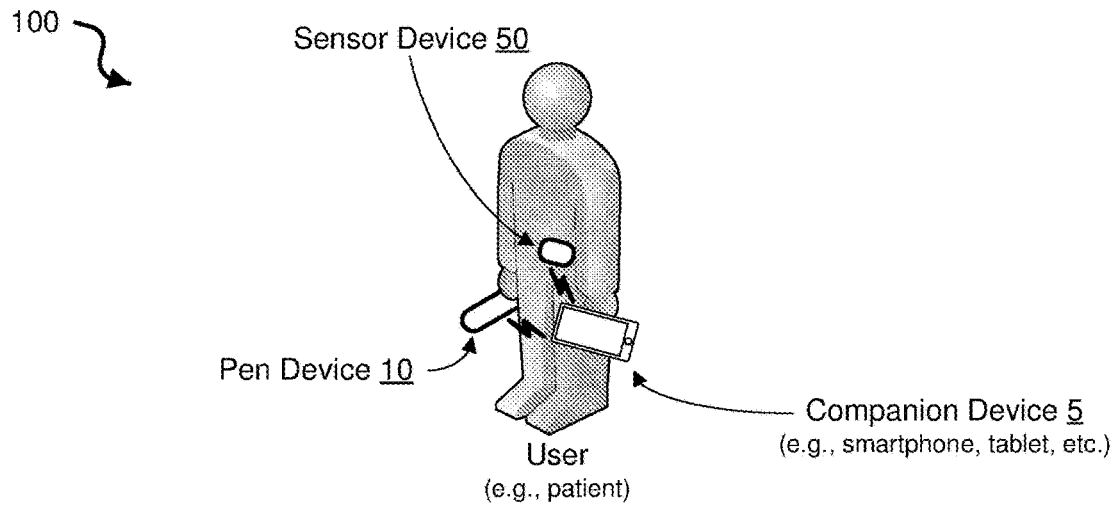
FIG. 1A shows a diagram of an example embodiment of an intelligent medicine administering system in accordance with the present technology.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

In addition to the challenges of tracking doses, calculating the right dose at the right time or under the right conditions is a widespread problem for patients of chronic conditions requiring daily dosing of medicine. Conventional dose calculators for administering insulin for Type I and Type II diabetes typically require manual estimation of carbohydrates ("carbs") at mealtime. For some users, carb counting and estimating may be too difficult, and some users may not utilize the dose calculator due to the manual work and number of steps required to do so, e.g., taking out one's smartphone, opening up an app, manually typing calculator inputs, etc.

Methods, systems and devices are described below for simplifying meal (e.g., carb) input, and for streamlining the process of getting a dose recommendation that may help improve both of these hurdles.

In some embodiments in accordance with the present technology, an intelligent medicine administering system provides medicine dose recommendation and management capabilities for Type I and Type II diabetes patients and their caregivers. In some aspects, the system includes a medicine injection device (e.g., insulin pen, also referred to as a "pen" or "pen device"), in wireless communication with a patient's companion device (e.g., smartphone). The companion device includes a software application ("app") having a dose calculator and decision support modules to calculate and recommend the dose of a medicine (e.g., insulin) the patient should administer using the wirelessly connected medicine injection device, as well as to provide control over several functionalities of the injection device, e.g., such as monitoring and recording dose sizes dialed on the injection device.

Communication between the pen device and the companion device provides the ability for dose tracking, logging, calculating, recommending, and/or communicating dose data with a user (e.g., patient user, health care provider (HCP) and/or caregiver), and other advantages of the intelligent medicine administering system. For example, each bolus that is dispensed by the pen device can be automatically logged and communicated to the companion device.

FIG. 1A shows a diagram of an example embodiment of an intelligent medicine administering system 100 in accordance with the present technology. The system 100 includes a pen device 10 in wireless communication with a mobile computing and communication device 5 of a patient user, also referred to as the user's companion device. The pen device 10 is operable to select, set and/or dispense a dose of the medicine for dispensing. In some implementations, the companion device 5 includes a smartphone, tablet, and/or wearable computing device, such as a smartwatch, smartglasses, etc. In some implementations, the companion device 5 is in communication with other computing devices, such as a laptop and/or desktop computer, a smart television, or network-based server computer. The companion device 5 includes an app associated with the pen device 10 of the intelligent medicine administering system 100, which can monitor and/or control functionalities of the pen device 10 and to provide a dose calculator and/or decision support modules that can calculate and recommend a dose of the medicine for the patient user to administer using the pen device 10.

The companion device 5 can be used to obtain, process and/or display contextual data that can be used to relate to the patient user's health condition, including the condition for which the pen device 10 is used to treat. In an illustrative example, the companion device 5 is operable to track the patient user's location; the patient user's physical activity including step count, movement distance and/or intensity, estimated calories burned, and/or activity duration; and/or the patient user's interaction pattern with the companion device 5. The app associated with the system 100 can aggregate and process the contextual data to generate decision support outputs to guide and aid the patient user in using the pen device 10 and/or managing their behavior to promote better health outcomes in treating his/her health condition.

In some embodiments, the system 100 includes a sensor device 50 to monitor one or more health metrics of the patient user. Examples of health metric data monitored by the sensor device 50 include analytes, such as glucose, heart rate, blood pressure, user movement, or other. In some implementations, the sensor device 50 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 5, which processes, stores and displays the continuous glucose values for the patient user.

Figure 1B:
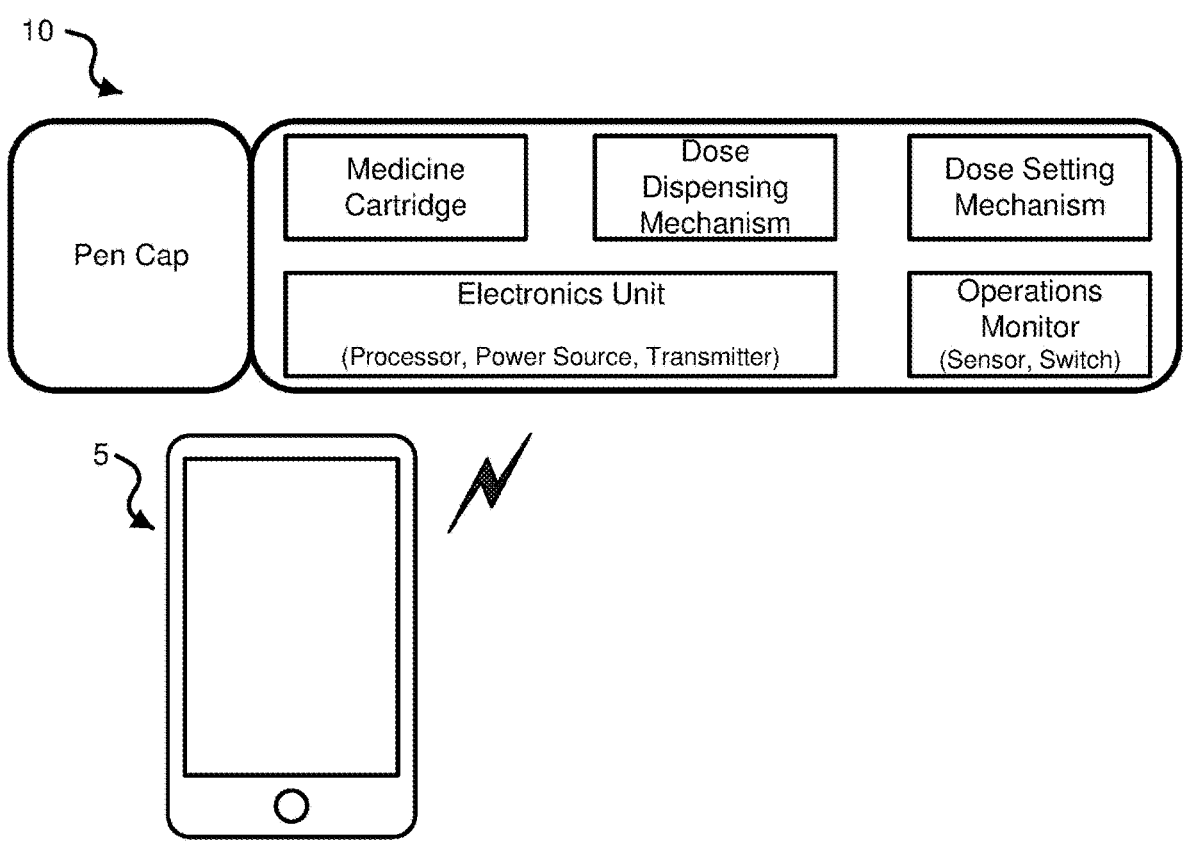
FIG. 1B shows a diagram of an example embodiment of a pen device of the intelligent medicine administering system of FIG. 1A.

FIG. 1B shows a diagram of an example embodiment of the pen device 10 of the intelligent medicine administering system 100. The pen device 10 is structured to have a body which contains the medicine cartridge (e.g., which can be replaceable). The pen device 10 is structured to include a dose dispensing mechanism to dispense (e.g., deliver) the medicine contained in the medicine cartridge out of the pen device 10; a dose setting mechanism to select and/or set the dose to be dispensed; an operations monitoring mechanism to determine that the pen device 10 is being operated and/or to monitor the operation of the dose being dispensed (e.g., such as a switch and/or sensor, or an encoder); and an electronics unit that can include a processor, a memory, a battery or other power source, and a transmitter.

The pen device 10 is configured in communication with a user's mobile computing and communication device 5, e.g., such as the user's smartphone, tablet, and/or wearable computing device, such as a smartwatch, smartglasses, etc., and/or a user's laptop and/or desktop computer, a smart television, or network-based server computer.

In some implementations of the system 100, for example, to use the pen 10, the user first dials up a dose using a dose knob. The dose knob of the pen 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen 10 to cause the pen 10 to begin to dispense the medicine, in which the quantity dispensed is in accordance with that set by the dose setting mechanism. In such implementations, the operations monitoring mechanism of the pen 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore by sensing rotation of the component, the movement of the drive shaft and the plunger is sensed. Movement of the encoder may be detected as data processed by a processor of the electronics unit of the pen 10, which can be used to measure the dose. In some implementations, the processor can then store the size of the dose along with a time stamp for that dose. In some implementations, the pen 10 can then transmit the dose and related information to the companion device 5. In such implementations when the dose is transmitted, the data associated with the particular transmitted dose is marked in the memory of the pen 10 as transmitted. In such implementations if the dose was not yet transmitted to the companion device 5, then the data associated with the dose will be transmitted at the next time a successful communication link between the pen 10 and the companion device 5 is established.

The operations monitor mechanism of the pen 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen 10 can include a manually powered mechanism or a motorized mechanism.

In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism can be operated over a much longer period of time, e.g., to better match the dynamics of carbohydrates, which can be like an extended bolus with a pump.

The software application (app) of the companion device 5, associated with the pen device 10, provides a user interface to allow the user to manage his/her health related data. In some implementations, for example, the companion device 5 can be configured to control some functionalities of the pen device 10. In some implementations, for example, the companion device 5 includes the user's existing smartphone, tablet, or wearable computing device. In some implementations, for example, the companion device 5 is an independent portable device that the user may carry on his/her person. In one example embodiments of an independent portable companion device 5, the companion device 5 includes a data processing unit, wireless communication unit to allow the device to communicate with the pen device 10, and a display unit.

Figure 1C:
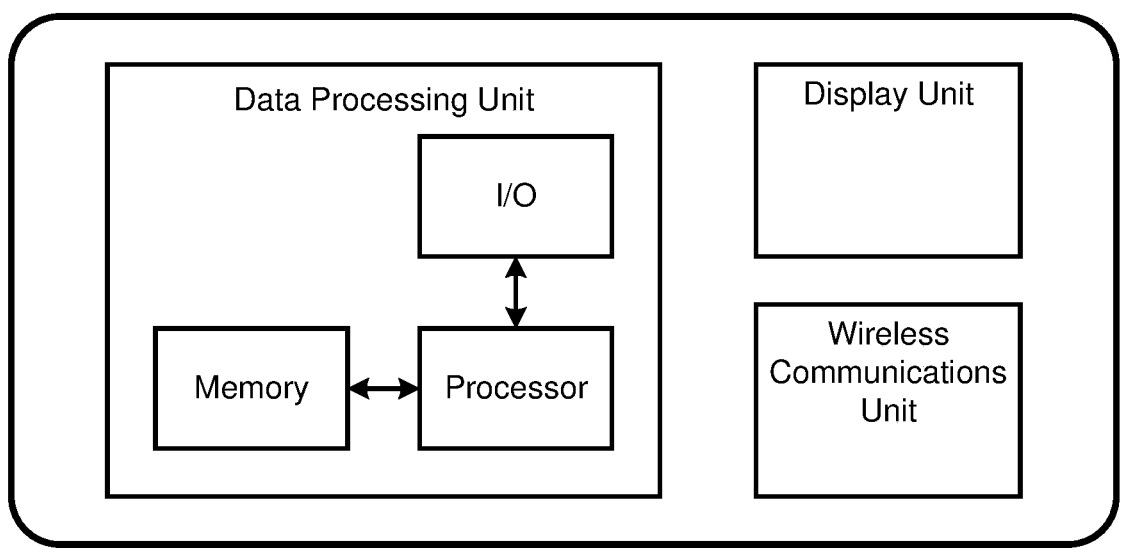
FIG. 1C shows a block diagram of an example embodiment of the companion device of the intelligent medicine administering system of FIG. 1A.

FIG. 1C shows a block diagram of an example embodiment of the companion device 5 of the intelligent medicine administration system 100. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the software application of the disclosed technology for health management. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In various operations of the disclosed intelligent medicine administration systems, for example, when a dosing event (e.g., an amount of fluid is dispensed from the pen device 10), a time stamp associated with the dispensing is referenced is recorded by the processing unit of the pen 10 (e.g., stored in the memory of the pen 10). For example, the time stamp may be the current time or a time where a count-up timer is used. When the dose information is eventually transmitted to the companion device 5, the time stamp and/or a 'time-since-dose' parameter is transmitted by the pen 10 and received by the companion device 5 and stored in the memory of the data processing unit of the companion device 5. In some implementations, for example, the time of the dose can be determined without the pen having to know the current time. This can simplify operation and setup of the pen 10. In some implementations, for example, a user time is initialized on the pen 10 from the companion device 5, in which the user time is used for dose time tracking. Using the system 100, the companion device 5 can know the time of the dose relative to the current time.

Once the companion device 5 receives the dose related information (e.g., which can include the time information and dose setting and/or dispensing information, and other information about the pen 10 related to the dosing event), the companion device 5 stores the dose related information in memory, e.g., which can include among a list of doses or dosing events. For example, via the software application's user interface, the companion device 5 allows the patient to browse a list of previous doses, to view an estimate of current medicament active in the patient's body ("medicament on board") based on calculations performed by a medicine calculation module of the software application, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Figure 1D:
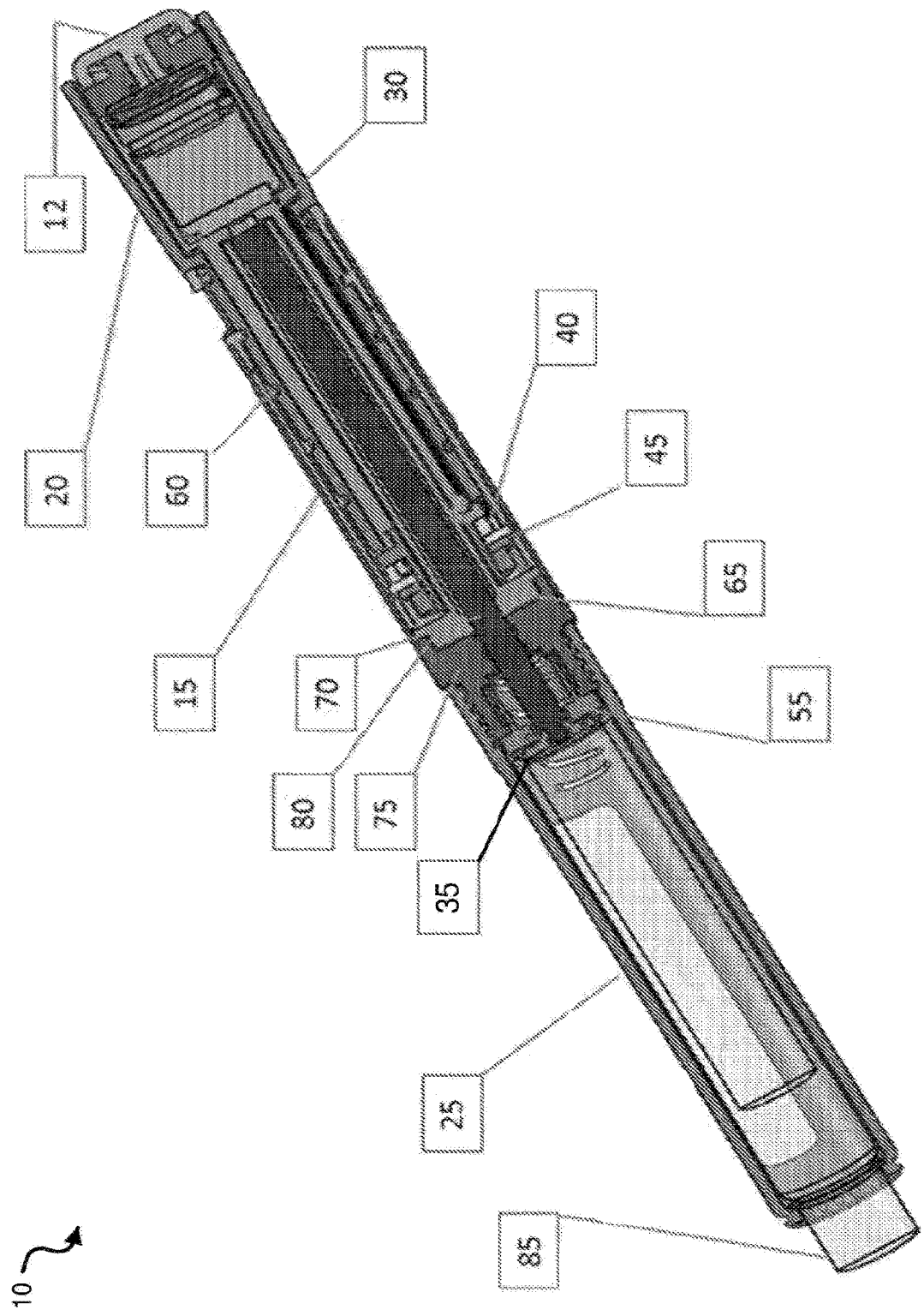
FIG. 1D shows a schematic illustration of an example embodiment of the pen device shown in FIG. 1B.

FIG. 1D shows a schematic illustration of an example embodiment of the pen device 10. The example shown in FIG. 1D illustrates the structural arrangement and interaction of the example modular units and mechanisms depicted in FIG. 1B for various operations of the pen device 10. As shown in FIG. 1D, the pen device 10 includes a mechanism to actuate a force to cause a displacement of a piston which resides within a medicament vial or cartridge 85. The displacement of the piston of the medicament vial 85 forces a volume of the medicament (that is proportional to the displacement of the piston) out of the vial 85, e.g., allowing it to be injected into a patient. The vial 85 is held within a medicament housing 25 of the pen device 10. The medicament housing 25 attaches to a main body housing 15 of the pen device 10, which includes a dose setting and dispensing mechanism and electronics unit of the pen device 10. In some embodiments, for example, the medicament housing 25 and the main body housing 15 may be a singular housing structure. The medicament housing 25 is structured to include a chamber to hold and/or encase the medicament vial 85 within the housing 25 of the pen device 10. The pen device 10 can also include a detachable pen cap (not shown) to cover an end of the pen device 10 that exposes a needle assembly (not shown) of the pen device 10 to disburse the medicine out of the pen device 10 when dispensed from the vial 85. The pen device 10 can include a vial spring 35, which provides a force on a screw retractor 55 to push the medicament vial 85 into the medicament housing 25 to ensure good dose accuracy. The pen device 10 includes a dose knob 20 attached to or included as part of the housing 15, where the dose knob is coupled to the housing by a non-self-locking thread 60. In some embodiments, for example, an electronics housing 30 may reside within the dose knob 20, in which the electronics housing 30 contains the electronics unit of the pen device 10. The dose setting mechanism includes a dose knob 20. When the dose knob 20 is rotated into or out of the housing 15 to adjust the dose, the electronics housing 30 does not turn. However, when translational or axial force is placed to the dose button 12 (e.g., in which resides the electronics housing), a catch structure component is engaged to lock the electronics housing 30 and dose knob 20 together, forcing them to rotate together as the pair travel back into the housing 15 upon actuation of the dose dispensing mechanism to apply force to the dose knob 20 to cause dispensing of the set dose. The rotation of the dose knob 20, e.g., which can be via the electronics housing 30, rotates a shaft 65 (e.g., which can be configured as a bi-directional clutch shaft). The shaft 65 in turn rotates a dose screw 70 which rides within a nut 75 which is fixed to the housing 15. This rotation causes the dose screw 70 to extend out of the housing 15 causing an injection of medicament. In some embodiments, for example, the dose dispensing mechanism can include a friction-causing structure 80, e.g., which can be coupled to the exemplary bi-directional clutch shaft 65 to present a frictionous surface (i.e., a surface that provides friction) to make contact with the nut 75 or housing body 15 or other internal structure of the dose dispensing mechanism, which acts from the bi-directional clutch shaft 65 to the housing 15 or nut 75 to prevent rotation of the shaft 65 while the dose setting mechanism is being adjusted via turning of the dose knob 20, but also allowing the friction to be overcome during the dose dispensing operation. In addition, by overcoming friction in the opposite direction the dose screw 70 may be driven back into the housing 15 and prepared for a new cartridge of medicament to be loaded. In some embodiments, for example, the pen device 10 includes a screw retractor component 55 that is axially fixed to the housing but rotationally free. The screw retractor component 55 is operable to be bent in to "grab" the non-circular cross section of the dose screw 70 allowing it to be rotated relative to the housing 15 and driven back into the housing 15. In some implementations, for example, the components of the pen device 10 could be manufactured by injection molding, machining or other similar process. In embodiments including the bi-directional clutch shaft, for example, the pen device 10 is capable of allowing retraction of the lead screw, and repeatability of operation of the dose dispensing mechanism.

In some embodiments, the sensor unit of the pen device 10 includes a rotational encoder, for example, between the dose knob 20 (e.g., which can be coupled to the jack screw) and the housing 15, and in electrical communication with the electronics unit contained in the electronics housing 30. The encoder is included in a sensor unit to determine the quantity of the dose set by the dose setting mechanism, and/or, the quantity of the dose dispensed by the dose dispensing mechanism. In some implementations, for example, the encoder can be configured in the pen device 10 to determine the dispensed dose by detecting rotation of the lead screw which is correlated with displacement of the pusher foot which is correlated with displacement of the receiving plunger in the vial 85, which in turn is correlated with dispensed insulin. In some embodiments, for example, the encoder can include two flat plates with contacts in between them. The plates are aligned perpendicular to the axis of the device. For one plate, a contact plate 40 is rotationally fixed to the jack screw, e.g., which can be via the electronics housing 30; and for the other plate, a code wheel 45 is rotationally fixed to the housing 15. In implementations, for example, when relative motion occurs between these two plates during dosing, the relative motion is measured and transmitted to the data processing and communications unit for processing, storage and/or transmission to the companion device 5.

In some embodiments of the pen device 10, for example, the dose setting and dispensing mechanism may include a mechanism in which the dose screw 70 is comprised of an elongate nut which screws in and out of the housing to provide dosing. The nut component in the previous described embodiment (e.g., nut 75) can include a separate screw structure; whereas in this embodiment of the dose screw, the nut component is part of the dose screw including exterior threads and is coupled to the housing 15. When the exemplary bi-directional clutch shaft 65 provides rotation, it operates on the jack screw, e.g., in which the dosing nut in this case threading it out of the housing.

Example embodiments and implementations of the disclosed intelligent medicine administration system are described. While the disclosed embodiments described herein are primarily based on diabetes management systems and methods involving insulin pen and glucose monitoring devices to facilitate understanding of the underlying concepts, it is understood that the disclosed embodiments can also include treatment of other health conditions using other medications by the pen device and/or monitoring of other analytes by sensor devices.

Dose Calculator and Decision Support Modules for User Management of Meal Inputs and Dosing Decisions In some aspects, the intelligent medicament delivery system 100 includes a streamlined dose calculator and decision support modules to determine and recommend a time- and circumstance-relevant dose of medicine (e.g., insulin) for the patient user associated with meal inputs and/or detected meal, exercise, or other user events. In some implementations, dose data is determined and can be provided by the app on the companion device 5 to the pen device 10 to set a recommended dose. The intelligent medicament delivery system 100 is able to provide the time- and circumstance-relevant dose of insulin based on real-time knowledge of glucose levels, e.g., provided by the example glucose sensor device 50 such as a CGM or smart blood glucose meter (e.g., smart BGM), and knowledge of insulin on board (IOB), e.g., provided by the pen device 10. In some examples, IOB can additionally or alternatively be provided by an insulin pump being used by the patient user, e.g., as some diabetic patient users may choose to alternative insulin pump use with an insulin pen for a time being and/or use an insulin pen as a supplement medication delivery device to the insulin pump.

Figure 2:
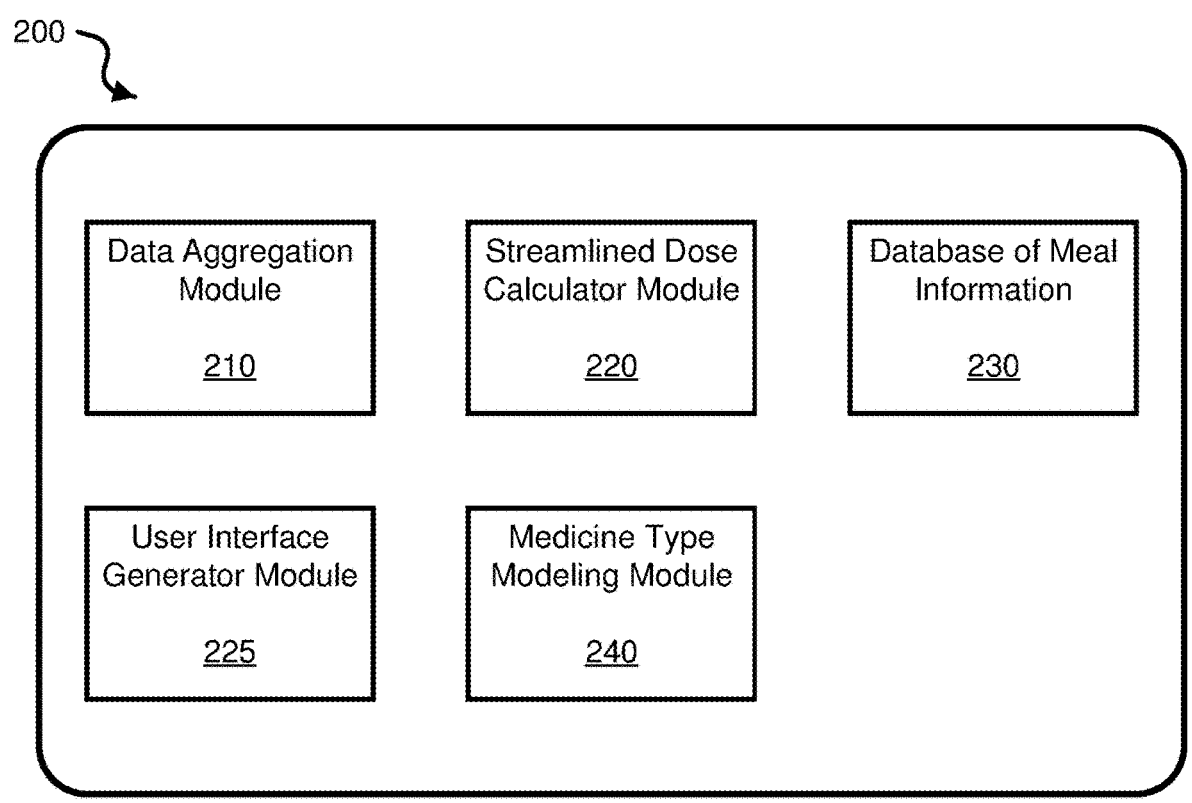
FIG. 2 shows a diagram of an example software architecture of data processing modules in accordance with some example embodiments of the system.

FIG. 2 shows a diagram of an example software architecture of data processing modules in some example embodiments of the app of the intelligent medicine administrating system 100. The diagram depicts an example software architecture 200 for processing health metric data and contextual data obtained by the app on the companion device 5, from the pen device 10, from the sensor device 50, and/or from other devices of the patient user and/or apps on the companion device 5. In some embodiments, the software architecture 200 is embodied as part of the app resident on the companion device 5. Similarly, in some embodiments, for example, the software architecture 200 can be embodied as part of a data processing system in the cloud (e.g., resident on one or more cloud computers). In some embodiments, the software architecture 200 is embodied as part of both the software app on the companion device 5 and the data processing system in the cloud, in which some or all of the modules of the software architecture 200 are shared or divided among the app on the companion device 5 and the data processing system in the cloud.

The software architecture 200 includes a data aggregator module 210 to obtain the health metric data from a device, such as the pen device 10, sensor device 50, and/or other devices or apps in communication with the companion device 5. The software architecture 200 includes a streamlined dose calculator module 220 to autonomously calculate a dose of the medicine associated with dose injections from the pen device 10 based on time-relevant and context- or circumstances-relevant data that is specific to the patient user of the pen device 10. Autonomous calculations by the streamlined dose calculator module 220 performs the dose calculations without user input. The software architecture 200 includes or is in communication with a database to store the health data and contextual data associated with the patient user and populations of patient users. The example modules shown in the software architecture diagram 200 can be organized to provide data to one another in various ways, including directly (e.g., module-to-module) and/or indirectly (e.g., via an intermediary module), based on a periodic, an intermittent, and/or a per-request basis. The software architecture 200 includes a user interface generator 225 that produces a user interface displayable by the app of the intelligent medicine administrating system 100 on a display of the companion device 5 and/or the pen device 10. In some implementations, the user interface generator 225 is configured to always display the calculated dose (also referred to as the recommended dose) determined by the streamlined dose calculator 220. In some implementations, for example, the recommended dose can be always displayable when the app is operating in foreground or in background mode, so that the display is able to present the recommended dose whether the user is actively using the system 100 app or not. In examples where the companion device 5 includes widgets or other complications displayed on the screen, the user interface generator 225 can produce the recommended dose as a widget or complication. In some implementations, for example, the 'always available' or 'always on' dose display can be a default setting, where the app allows a user to switch the always display off for certain time periods or indefinitely, until switched back to always available.

In some embodiments, the software architecture 200 can include a meal information database 230, which can be a database in the cloud, in communication with the software app on the companion device 5 to store information about meals to be accessible to the various modules of the software app. In some implementations, the software architecture 200 includes a meal information module to receive and/or store at least some meal information provided from the meal information database 230 and/or from the data aggregator module 210.

It is noted that while the app is described as resident on the companion device 5, it is understood that some or all of the software modules of the app may be resident on the pen device 10 or in a centralized networked computer server, e.g., the cloud, and may be distributed across multiple locations.

Streamlined Dose Calculator Module

In some implementations, the app of the companion device 5 is configured to operate in an "always available" or "always on" mode, or in other words, "not-turned-off", in which the streamlined dose calculator module 220 is continuously or semi-continuously (e.g., intermittently) calculating an appropriate dose of insulin based on the real-time health metric and contextual data of the patient user obtained by the devices of the system 100. For example, the companion device 5 would provide an 'always-available' display of insulin-related information (e.g., IOB, next recommended dose including dose amount, type of insulin and time of dose) that requires no specific action by the patient user to launch the streamlined dose calculator module 220 of the app on the companion device 5. For example, in such implementations, the user would not necessarily need to navigate the operating system of the companion device 5 and open the app in order to enter meal information, as the streamlined dose calculator module 220 would be operating to provide a display tool that displays the insulin-related information (and/or glucose-related information) and allows user input from the tool that is provided to the streamlined dose calculator module 220. In some example implementations, the display and input tool is manifested on the companion device 5, such as on a home screen of the companion device 5, an app screen, in the form of a notification or widget, and/or on an accessory device such as a smartwatch. In some example implementations, simply opening the app would display the relevant information provided by the streamlined dose calculator module 220, e.g., without requiring manual entry or settings selections using the app. Some examples of the display tool that requires no manual entry but continuously displays the calculated dose information, continuously and autonomously updated in real-time by the streamlined dose calculator module 220, are shown later in FIG. 3C. In some examples, the streamlined dose calculator module 220 autonomously calculates the dose of the insulin medicine intermittently or at regular intervals, e.g. such as every second, every minute, every five minutes, every fifteen minutes, every hour, or the like.

In some implementations, the app of the companion device 5 is configured to display dose recommendations based on contextual information, e.g., including time of day and location of the user. For example, suggestion of insulin doses the patient user takes around a lunchtime meal (referred to as "lunch doses") may appear at a pre-set lunch time, or based on the typical time the user takes a lunch dose based on a past dose history. The recommendation would persist on the display until the user takes the lunch dose, or the lunch time window passes, or the user manually confirms a meal or clears the recommendation. In another example, dose recommendations may be based on the user's location, such as providing a recommendation of insulin doses the patient user should take upon the user returning to his/her home in the evening time, e.g., from a prior location (which may be regularly left at the time in the evening, such as the user's work, school, or other activity in the user's lifestyle routines).

In some implementations, the alert may passively display or be available within an app at the beginning of a set time period (for example, typical lunch time), but may actively alert the user with a sound, vibration, or other notification at the end of the set time period, indicating that the user may have forgotten to dose.

In cases where the user consumes a meal and forgets to inject the recommended insulin dose until they are reminded by a notification, their blood glucose may have already begun to rise due to the ingested meal. If this is the case, calculating a recommended dose based on their current (elevated) glucose level and the amount of carbs consumed at the meal would result in too large of a recommendation, since the dose would be covering the carbs and also compensating for the elevated glucose level. This is likened to double-counting the carbs, since some insulin is recommended based on the number of carbs, and more insulin is recommended to reduce the patient's glucose level that was elevated due to these same carbs. To account for this, the carb amount or the glucose level can be compensated to avoid the double-counting. Herein, glucose levels or values may be referred to as "BG" levels or values.

To compensate for the change in BG value, for example, the following methods may be used. If the user has a CGM or other past BG data logged, the user may manually indicate the actual time (or time ago) of the meal, and their BG value near the time of the meal can be used for the calculation rather than their present BG value. Alternatively, for example, if the user does not log a specific time of the meal, CGM data can be evaluated retrospectively. The average BG value from the set time window for the meal can be used for the calculation. Alternatively, for example, the minimum BG value from the set time window for the meal can be used. Alternatively, for example, the minimum or average BG value can be taken from a pre-set past window of time, e.g., the past hour. Alternatively, for example, a recent rise in BG data can be algorithmically identified, indicating the effect of the meal increasing BG, and the BG value from before this upward rise can be used. In all of these example cases, if the present BG value is lower than the compensated value, the present lower BG value should be used for safety, to avoid recommending too large of a dose. The goal of compensation is to account for a BG value elevated by recent food, but if the BG has dropped, then that indicates that food has not increased it and compensation is not necessary.

To compensate for the meal carbs, for example, the following methods may be used. If the user manually indicates the actual time (or time ago) of the meal, the carb amount can be discounted based on elapsed time. There may be an initial period (e.g., 30 minutes) where no effect on BG is expected, and no compensation is performed. Then based on a pre-set time (which may be based on the user and/or the specific type of food), the carb amount is reduced to account for carbs presumed to have been metabolized already, and already affecting the user's present BG value. This can be a linear burndown (e.g., assuming 10% of the meal is metabolized per 10 minutes) or an exponential or other nonlinear mathematical relationship similar to the exponential burndown of insulin in the body used to calculate IOB.

If the user does not manually specify the time of the meal, it can be presumed based on the pre-set meal time window, or based on a pre-set past window of time for a missed dose (e.g., any time a missed dose reminder occurs, it may be presumed that the patient ate 1 hour prior.) The time of the meal could also be algorithmically estimated based on CGM data, presuming that the meal was eaten before a recent BG increase. The time since the increase in BG can be used to discount the carb amount. For example, if BG began increasing 20 minutes prior to the calculation, the carb amount may be proportionally discounted based on 20 minutes of metabolism and effect on BG. There may also be a pre-set discounting percentage for any missed-dose reminders. For example, if a meal dose would otherwise have been calculated as 10 units at the time of the meal, if the missed-dose reminder occurs this recommendation may be reduced by a set percentage (e.g., 20%) such that a reduced recommendation (for example 8 units) would be provided with the assumption that some amount of time had likely passed since the user ate the meal.

The streamlined dose calculator module 220 is configured to display one or more of the following: (a) current correction insulin dose (or food to eat) to reach target assuming no meal is planned; and/or (b) current dose calculation for a meal. For instances of the current dose calculation for a meal, the calculated dose determined by the streamlined dose calculator module 220 can be based on a fixed (pre-set) meal size, which is assumed based on contextual data including user location (e.g., patient user at a particular restaurant, home, etc.), time of day, recent meal information, and historical meal information including determined meal patterns. For example, multiple recommended doses can be listed to the patient user based on a type of meal such as a "snack" or a "small", "medium", or "large" meal. The calculated dose determined by the streamlined dose calculator module 220 can be based on doses for the patient user's common meals previously entered, e.g., which may be based on location, time of day, or other similar factors to provide the most relevant suggestions. The calculated dose determined by the streamlined dose calculator module 220 can be based on doses for common menu items at a restaurant, e.g., even if the user has not dined there before. For example, this may be based on the user's typical meal types and sizes, to provide personalized recommendations. This may also serve as a health recommendation, suggesting healthier lower-carb options available at a particular location.

The streamlined dose calculator module 220 can produce the display and input tool on the companion device 5 where any of the above examples may be listed together. In an illustrative example, the display and input tool can list three recommended doses corresponding to a "small" meal, "medium" meal, and "large" meal, respectively, and/or list a recommended dose based on a pre-set meal (such as a routine meal the patient user may always have at a certain time, location, etc.). After a meal is logged (and/or a meal dose is taken), the suggested meal types may change. For example, instead of typical meal sizes, it may offer updated options such as a second helping, a small dessert, or a large dessert, aligned with additional carbs that may commonly be consumed following a meal.

In some implementations, the display and input tool of the streamlined dose calculator module 220 can allow the user to explicitly confirm a meal (e.g., which may include confirming the meal size and/or type) in the user interface of the app, via the companion device 5. In this case, the confirmation of the meal (e.g., possibly including its size and/or type) is logged in a patient data database of the system 100, upon which the streamlined dose calculator module 220 continues automatic recommendations updated accordingly.

In some examples, if a user does not explicitly confirm a meal, it may be implicitly confirmed by the streamlined dose calculator module 220. For example, a dose of insulin taken near mealtime can be interpreted as confirmation of a meal. In the case of a range of dose suggestions provided to the user (e.g., such as different values for a small, medium, or large meal) if the user take a dose equal or nearly equal to one of the recommendations, the streamlined dose calculator module 220 may infer that the corresponding meal size was eaten. This can be qualitative, such as inferring that the user ate a "small" or "large" meal based on the recommendations. Or in the case where the streamlined dose calculator module 220 presents multiple options based on carbs in the meal, the dose taken can be interpolated or extrapolated to infer the number of carbs the user was accounting for. For example, if the calculator states that 2 units should be taken for a 10 carb meal and 4 units should be taken for a 20 carb meal, but the user actually doses 3 units, the streamlined dose calculator module 220 may interpolate that the user ate a 15 carb meal. Or with the same recommendations if the user actually doses 6 units, the streamlined dose calculator module 220 may extrapolate that the user ate a 30 carb meal.

The recommended dose(s) may be viewed by the patient user on the companion device 5 by scrolling through multiple suggestions provided by the streamlined dose calculator module 200 via the 'always-available' display tool. In some implementations, a simple confirmation by the patient user (e.g., button press on the companion device 5 or pen device 10) can log the selected meal or meal type into a database associated with the patient user, e.g., which can be part of the app and/or in the cloud.

For a period after eating (e.g., 2 hours) there are unmetabolized carbs in the body that are not typically accounted for by a dose calculator that only considers BG, IOB, and carbs currently being eaten. In some implementations of the streamlined dose calculator module 220, to prevent inaccurate recommendations that do not account for unmetabolized carbs, the display may be disabled for some time period after a meal is consumed. Alternatively, for example, the calculator may allow for carb correction doses only, omitting BG and IOB from the calculation. In a further embodiment, the carbs logged may be accounted for with an estimated burndown, such that the amount of still unmetabolized carbs can be estimated. The estimated unmetabolized carbs can be used to estimate a future glucose response, or can be used to estimate the insulin needed to cover them—either way, providing an accurate dose calculation that accounts for the carbs from the previous meal.

The burndown time for carbs can be a setting that a user or physician selects (such as 2 hours, for example, for all meal types). Alternatively, the calculator may adjust this value based on the nutritional content of food. For example, orange juice may have a rapid burndown and BG response, and pizza may result in a more prolonged burndown BG response.

In some implementations, the app of the companion device 5 is configured to operate in a pre-set fixed-dose therapy schedule, as defined by a physician. In such implementations, for example, the user may receive reminders, via the companion device 5 and/or pen device 10, when he/she has not taken a recommended dose by the streamlined dose calculator module 220 in accordance with the pre-set fixed-dose schedule, and/or when some details of insulin taken is recorded, but further details such as meal sizes is needed by the streamlined dose calculator module 220 (or other modules of the app).

Figure 3A:
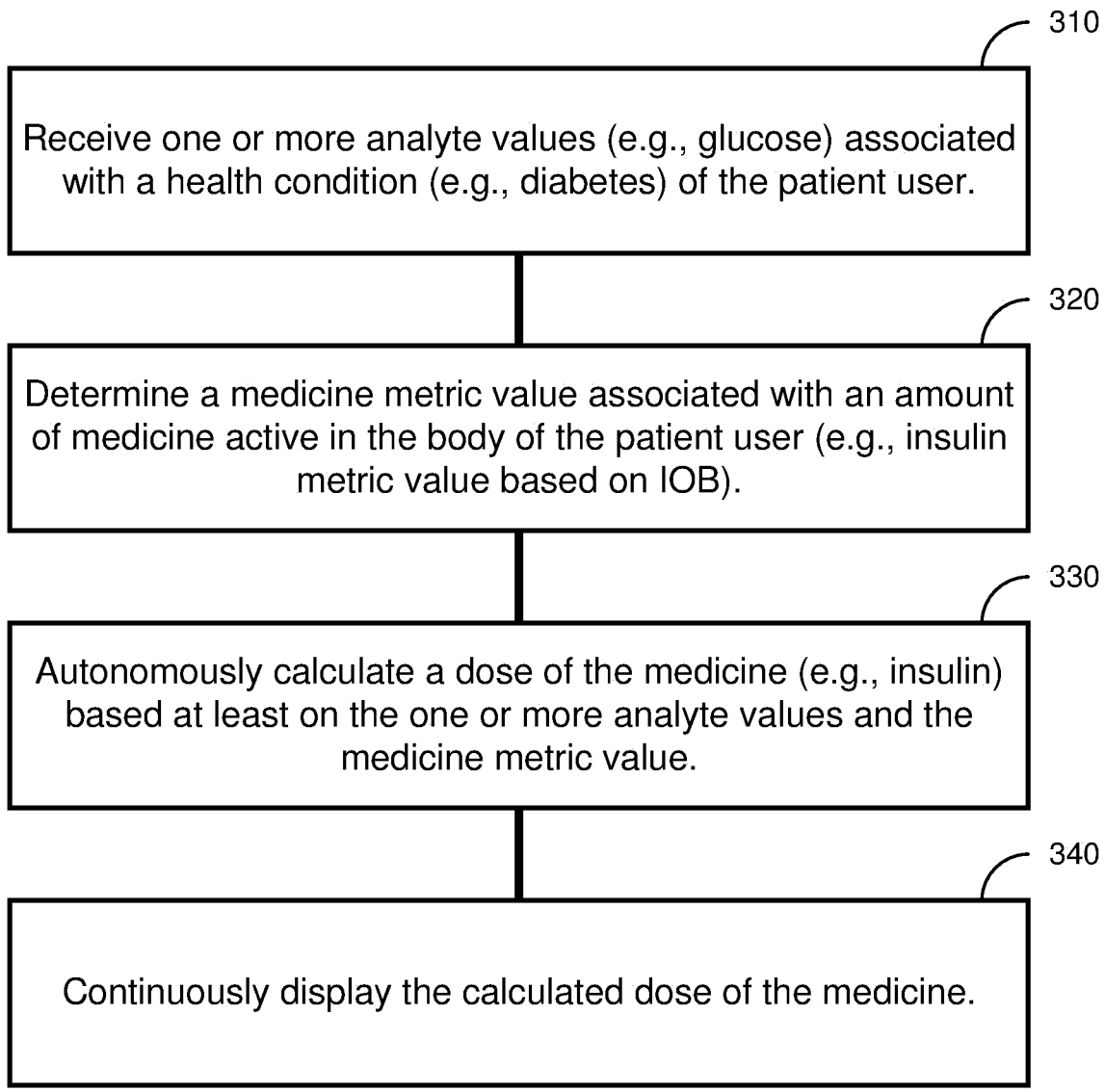
FIG. 3A shows a flow diagram of a method for determining a dose of a medicine, such as insulin, for the patient user in accordance with some embodiments of the disclosed technology.

FIG. 3A shows a flow diagram of a method 300 for determining a dose of a medicine for the patient user in accordance with some embodiments of the disclosed technology. The method 300 includes a process 310 to receive, by the software app on the companion device 5, one or more analyte values (e.g., glucose values) associated with a health condition (e.g., diabetes) of the patient user. In some implementations of the process 310, for example, one or more glucose values can be received by the sensor device 50, such as the example CGM or connected BG device. The method 300 includes a process 320 to determine, by the software app on the companion device 5, a medicine metric value associated with an amount of medicine active in the body of the patient user, e.g., such as an insulin metric value based on IOB. In some implementations of the process 320, the medicine metric value is determined by the app based on data associated with dispensed doses administered by the pen device 10. For example, in some implementations, the process 320 includes autonomously calculating the insulin metric value is based on IOB data using one or more previous doses of an insulin medication administered to the patient user, including a dose amount, a type of the insulin medication, and a time of administration of the previous dose. Whereas in some implementations, for example, the medicine metric value is received by the app from another application (e.g., health aggregation app, such as Apple Healthkit or Google Health or the like) or from another medicine delivery device (e.g., insulin pump) and authenticated in the process 320. The method 300 includes a process 330 to autonomously calculate a dose of the medicine based at least on the one or more analyte values and the medicine metric value. The process 330 can include autonomously calculating the dose of the medicine (e.g., dose of the insulin medicine) using a predetermined calculation equation and/or calculation parameters. For example, a desired change in glucose level (e.g., decreasing a current BG of 200 mg/dL to a target of 120 mg/dL would mean a desired change of −80 mg/dL) is multiplied by the user's Correction Factor to determine the amount of insulin required to adjust BG from the current level to target. In addition, the grams of carbohydrate to be eaten are multiplied by the user's Carb Factor to determine the amount of insulin required to compensate for the meal. These two insulin amounts are summed along with any current insulin in the patient user's body (Insulin on Board, or IOB) to determine the final dose recommendation. The method 300 includes a process 340 to continuously display, on a display of the companion device 5 and/or the pen device 10, the calculated dose of the medicine.

Implementations of the method 300 can include one or more of the following example features. For example, the calculated dose of the insulin medicine can include a next-recommended dose of the insulin medicine including a dose amount, a type of insulin and a time of dose. For example, the calculated dose of the insulin medicine can be associated with a current correction insulin dose to reach a target glucose level. In some implementations, the method 300 can further include receiving (e.g., from the companion device 5) contextual data associated with the patient user, in which the obtained contextual data includes information pertaining to one or more of a measured heart rate of the patient user, a measured blood pressure of the patient user, a physical activity including at least one of an activity or exercise by the patient user, a location of the patient user, or a mental state of the patient user. In some implementations, for example, the method 300 can further include receiving (e.g., by the app of the companion device 5), contextual data associated with the patient user obtained by the mobile computing device, in which the obtained contextual data includes information associated with a meal (e.g., such as an amount of carbohydrates or calories). In some implementations, for example, the process 340 to continuously display the calculated dose can include displaying the calculated dose of the insulin medicine on a home screen, on an app screen, or in a form of a notification or a widget of the companion device 5 or pen device 10.

In some implementations, the method 300 can further include a process to generate an assumption associated with a carbohydrate metric of the patient user. Examples include a carbohydrate-to-insulin ratio, and/or an insulin correction factor. In such implementations, the process 343 includes autonomously calculating the dose of the insulin medicine based on the glucose value(s), the insulin metric value, and the generated assumptions associated with the carbohydrate metric(s) of the patient user.

Figure 3B:
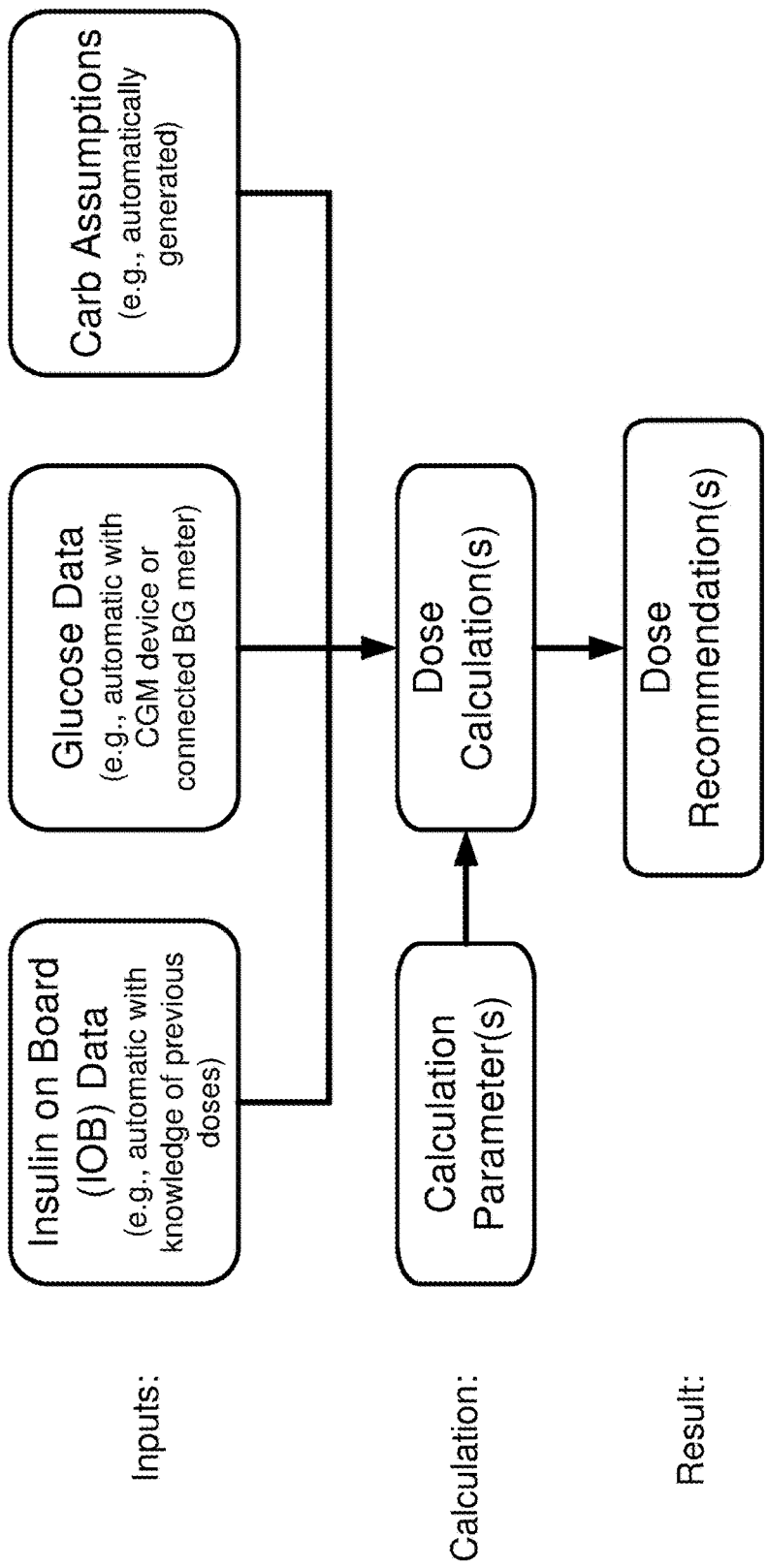
FIG. 3B shows a diagram illustrating an example implementation of the method of FIG. 3A for an 'always available' insulin medicine recommendation by a streamline dose calculator module in accordance with certain embodiments of the present technology.

FIG. 3B shows an example diagram illustrating an example implementation of the method 300 for an 'always available' insulin medicine recommendation by the streamline dose calculator module 220.

FIG. 3C shows an example diagram illustrating an example user interface for continuous display of the recommended dose of insulin medicine in an 'always available' implementation of the streamline dose calculator module 220. The example user interface can be continuously displayed on a home screen, on an app screen, or in a form of a notification or a widget of the companion device 5 or pen device 10. For example, in contrast with conventional devices for calculating a dose, where a user must input information to the device, which can include taking extra steps to open or launch a particular application in addition to typing or speaking inputs into the device with the input information. The example streamlined dose calculator module 220 can be implemented to provide the patient user with the important dosing information (e.g., amount of the medicine, type of medicine, and/or time to administer the medicine, etc.) in a manner that is always available to the user without requiring any input or additional action by the user.

Figure 4:
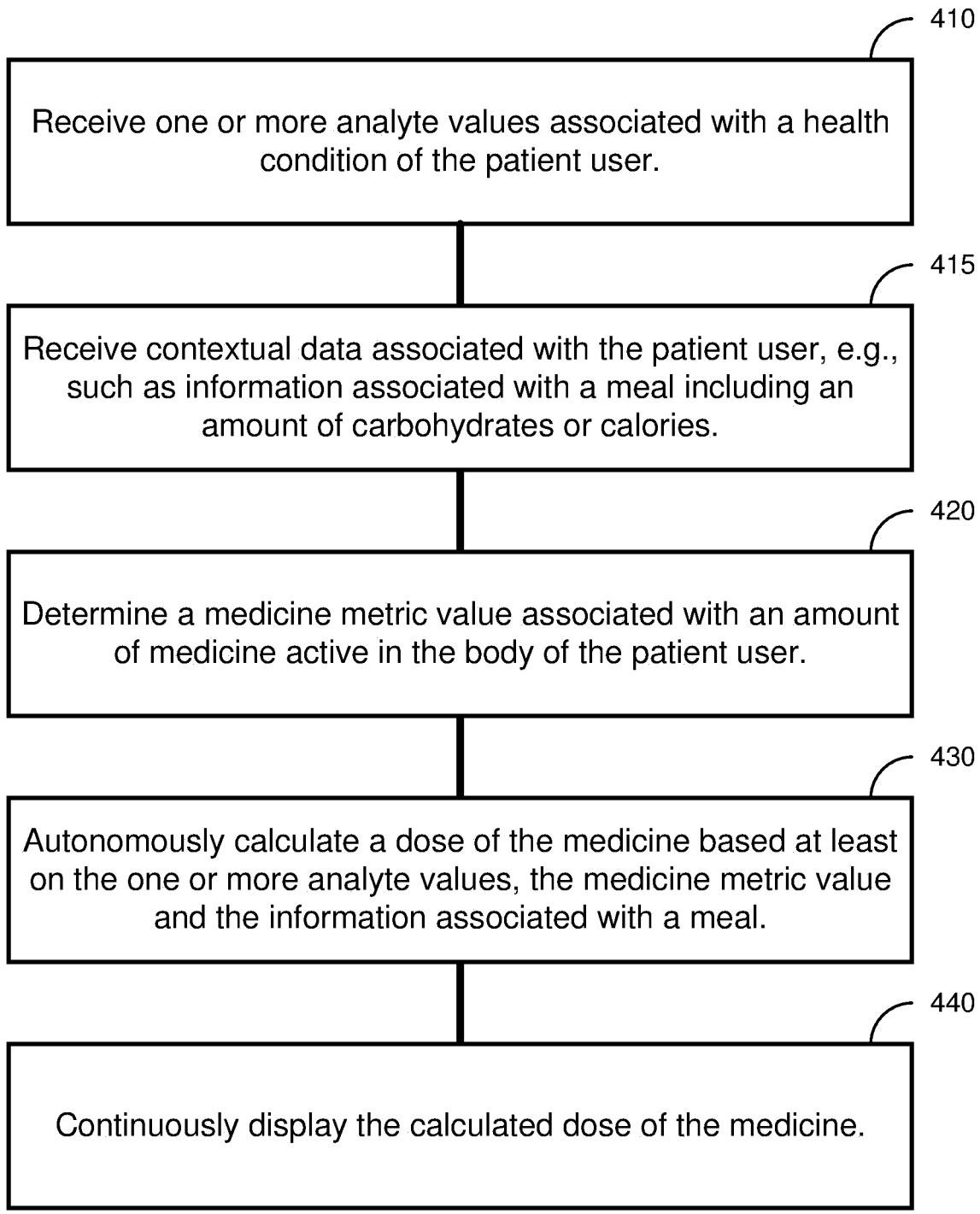
FIG. 4 shows a flow diagram of a method for determining a dose of a medicine for the patient user in accordance with some embodiments of the disclosed technology.

FIG. 4 shows a flow diagram of a method 400 for determining a dose of a medicine for the patient user in accordance with some embodiments of the disclosed technology. The method 400 includes a process 410 to receive, by the software app on the companion device 5, one or more analyte values (e.g., glucose values) associated with a health condition (e.g., diabetes) of the patient user. In some implementations of the process 410, for example, one or more glucose values can be received by the sensor device 50, such as the example CGM or connected BG device. Also, for example, in addition to glucose values, a glucose trend may also be considered. For example, a quickly rising glucose value may necessitate a larger insulin dose than if it were level, and a falling glucose value may require a smaller insulin dose. The method 400 includes a process 415 to receive, by the app, contextual data associated with the patient user that includes information associated with a meal (e.g., including at least one of an amount of carbohydrates or calories associated with the meal). The method 400 includes a process 420 to determine, by the software app on the companion device 5, a medicine metric value associated with an amount of medicine active in the body of the patient user, e.g., such as an insulin metric value based at least on IOB. In some implementations of the process 420, the medicine metric value is determined by the app based on data associated with dispensed doses administered by the pen device 10, whereas in some implementations, the medicine metric value is received by the app from another application (e.g., health aggregation app, such as Apple Healthkit or Google Health or the like) or from another medicine delivery device (e.g., insulin pump). The method 400 includes a process 430 to autonomously calculate a dose of the medicine based at least on the one or more analyte values, the medicine metric value and the information associated with a meal. The method 400 includes a process 440 to continuously display, on a display of the companion device 5 or the pen device 10, the calculated dose of the medicine. In some implementations of the method, the method 400 requires no user input action. For example, the information received associated with the meal can require no user input action by the patient user to initiate or launch the software application in order to input the information.

Implementations of the method 400 can include one or more of the following example features. In some implementations of the method 400, for example, the contextual data received by the app can further include information pertaining to one or more of a measured heart rate of the patient user, a measured blood pressure of the patient user, a physical activity including at least one of an activity or exercise by the patient user, a location of the patient user, or a mental state of the patient user. In some implementations, for example, the information associated with the meal includes a preset input indicative of a particular sized meal. Examples of the particular sized meal can include (i) a small meal including a first predetermined amount of carbohydrates or calories, (ii) a medium meal including a second predetermined amount of carbohydrates or calories, (iii) a large meal including a third predetermined amount of carbohydrates or calories, and/or (iv) a snack meal including a fourth predetermined amount of carbohydrates or calories. In some implementations, for example, the particular sized meal can be calculated by the software application based at least in part on a time of day, a recent meal eaten by the patient user, or historical meal information including a meal pattern. In some implementations, for example, the method 400 includes autonomously determining an amount of carbohydrates or calories for intake by the patient user; and displaying the determined amount of carbohydrates or calories. In some implementations, for example, the method 400 includes determining a subtype of the medicine to be dispensed by the injection pen device, in which different subtypes of the medicine differ in one or both of pharmacokinetics (PK) and pharmacodynamics (PD) of the medicine, and autonomously calculating the dose is further based on a PK-PD profile of the subtype of the medicine.

Complexity of the therapy can be tailored to the particular user's preferences, ability, and clinical need, as illustrated by the following examples. FIGS. 5A-5D show diagrams of an example user interface of a software application on a companion device for a single fixed meal dose, for fixed meal doses based on meal size or type, or for fixed meal doses based on meal type and size. FIGS. 6A-6D show diagrams of an example user interface of a software application on a companion device for a single fixed meal size estimation and for fixed meal sizes based on meal type, meal size, or a combination thereof. FIG. 7A shows a diagram of an example interface of a software application on a companion device for setting meal dose range based on meal size. FIGS. 7B and 7C show diagrams depicting example interfaces of a software application on a companion device for selecting meal dose on a sliding scale of meal size, with a smaller meal size selected and with a meal larger size selected, respectively. FIG. 8A shows a diagram of an example interface of a software application on a companion device for setting meal carb estimation range based on meal size. FIGS. 8B and 8C show diagrams depicting example user interfaces of a software application on a companion device for selecting meal carb estimation on a sliding scale of meal size, with a smaller meal size selected and with a meal larger size selected, respectively.

Figure 5A:
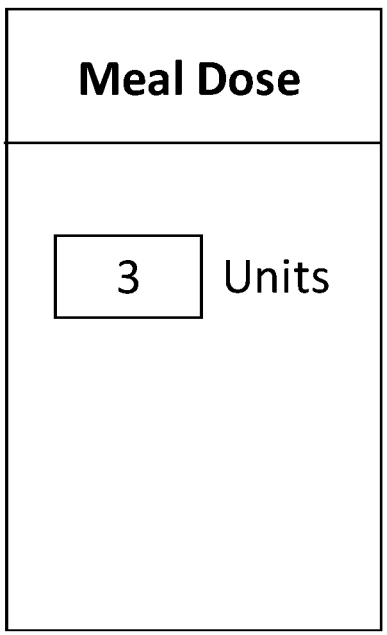
FIGS. 5A-5D show diagrams of an example user interface of a software application on a companion device for a single fixed meal dose and for fixed meal doses based on meal type, meal size, or a combination thereof.
Figure 5B:
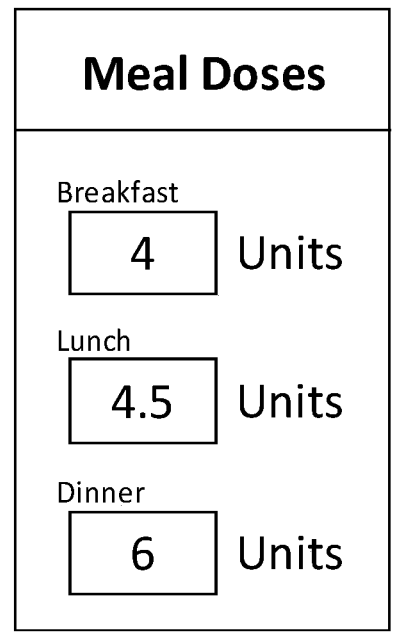
Figure 5C:
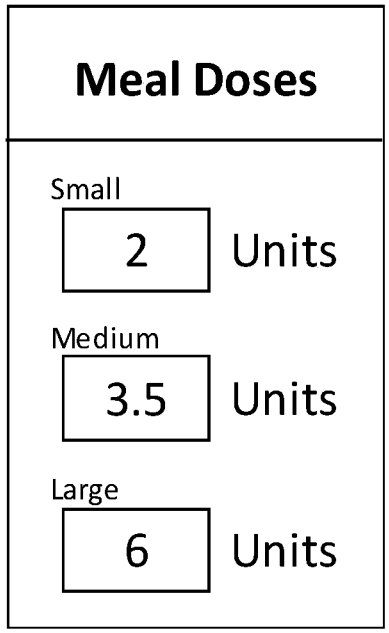
Figure 5D:
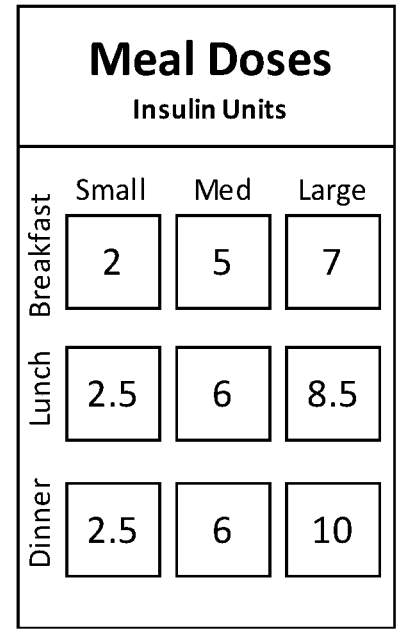

FIGS. 5A-5D show variations of example settings for fixed dose therapy. For example, FIG. 5A shows an example user interface for a single dose size for every meal; FIG. 5B shows an example user interface for variable dose sizes based on meal type, FIG. 5C shows an example user interface for variable dose sizes based on meal size; and FIG. 5D shows an example user interface for variable dose size based on meal type and meal size. These examples illustrate settings that may then be used to present the user recommendations based on their current context (for example, displaying the appropriate meal type based on time of day).

FIG. 6A-6D show variations of example settings for meal estimation therapy. For example, FIG. 6A shows an example user interface for a single fixed meal size estimation (e.g., a single carb amount for every meal); FIG. 6B shows an example user interface for fixed meal sizes based on meal type (e.g., variable carb amounts based on meal type); FIG. 6C shows an example user interface for fixed meal sizes based on meal size (e.g., variable carb amounts based on estimated meal size); and FIG. 6D shows an example interface for fixed meal sizes based on meal type and meal size (e.g., variable carb amounts based on meal type and size). These examples illustrate settings that may then be used to present the user recommendations based on their current context (for example, displaying the appropriate meal type based on time of day).

FIG. 7A-7C illustrate example user interfaces for sliding scale dose therapy, and FIG. 8A-8C illustrate example user interfaces for sliding scale meal estimation therapy. Bounds for dose size are set in the interface shown in FIG. 7A, and then the user may dynamically adjust a slider from "small" to "large" based on the size of their meal. FIG. 7B shows the slider at a smaller setting, and FIG. 7C shows the slider at a larger setting. Based on the qualitative setting of the slider, for example the software application can interpolate a recommended dose based on the set bounds. In a similar manner, for sliding scale meal estimation, bounds for carb amounts in a meal are set in the interface shown in FIG. 8A, and then the user may dynamically adjust a slider from "small" to "large" based on the size of their meal. FIG. 8B shows the slider at a smaller setting, and FIG. 8C shows the slider at a larger setting. Based on the qualitative setting of the slider, for example, the software application can interpolate a recommended dose based on the set bounds.

In some implementations, a newly diagnosed patient user may begin with a simple regimen, such as a single fixed size meal dose. This may be done to ease the mental burden of managing a new disease, and in some cases may be sufficient due to the early stage of the disease. But over time, the patient may be better served by more sophisticated regimens, possibly transitioning to variable meal sizes, and then carb counting. By monitoring the user's compliance with the existing mode of therapy, and their success achieving target BG after each dose is taken, it may suggest the appropriate time to advance to a more sophisticated method. In this way, the system can start a user with a simple regimen and gradually introduce them to more complexity within the same system without necessarily requiring a physician consultation, or alternatively presented as a recommendation to a physician to review and approve. For example, a patient beginning with fixed dose size therapy would be a candidate to advance to variable meal size therapy once they've used the system for a predetermined amount of time (e.g., 2 weeks) and have had good compliance (e.g., have taken three meal doses >90% of the days they have used the system). The system may also rate the success of fixed-dose therapy at achieving target BG values after a meal. By averaging the absolute difference between actual and target BG some time after each dose, e.g., as an absolute value (such as mg/dL) or a percentage, when it detects that the user is above a threshold of error it may suggest transitioning to a more sophisticated regimen, such as meal size estimation. For example, the user may be prompted to switch therapy if the delta from actual BG and target BG 2 hours after a dose is greater than 50 mg/dL, taken as an average over the past week. Similarly, after achieving success with meal dose size estimation, the user may be prompted to transition to carb estimation based on meal size.

Titration Dosing Mode

Titration is the gradual adjustment of parameters based on past user success, typically beginning with conservative values that will result in small doses and avoid hypoglycemia, gradually increased until the desired outcome is achieved. It can be applied to therapy parameters including fixed dose sizes, meal size estimates, insulin sensitivity factor, insulin to carb ratio, insulin action time, and carb metabolism time. Typically, these are performed by a physician or HCP at periodic visits, which are often months apart, and are based on incomplete data, relying on the patient's memory or subjective experience with the present therapy. By introducing an automated titration system as disclosed here, adjustments are based on exact insulin dosing data allowing better precision in the resulting adjustments, and can be done automatically by the system without requiring a physician visit, at a shorter time interval—adjusting the parameters as soon as sufficient data has been gathered, versus waiting for the next physician follow-up appointment. Or, if a physician manually adjusts values after confirmation and review, rather than allowing the system to make autonomous adjustments, they can be provided with precise calculations rather than subjective estimates as described above.

In some implementations, the app of the companion device 5 is configured to operate in a titration dosing mode. For example, the streamlined dose calculator module 220 can determine and recommend the time- and circumstancebased insulin dose using a clinically-based insulin titration scheme. In such instances, the streamlined dose calculator module 220 stores a titration protocol that is referred to for recommending fixed doses (i.e., not based on meal size) that are increased until the appropriate glucose value outcome is achieved. As with fixed-dose therapy, the system 100 can recommend appropriate doses per the titration, providing reminders and logging functions, but not requiring detailed meal information.

In some implementations of titration dosing mode, the system 100 can automatically monitor CGM data or connected blood glucose meter (BGM) data to automatically adjust dose amounts until the target response is reached. In some implementations, the system 100 could operate in an "open loop" mode to allow a physician or other HCP to adjust dose recommendations manually until the target response is reached. These adjustments could be made directly to the streamlined dose calculator on the companion device 5 itself, or remotely such as through the cloud from an Internet-connected and secure client computer via a web browser.

Figure 9:
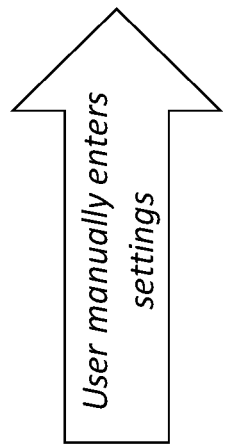
FIG. 9 shows an illustration depicting a paper prescription form with a section matching the patient user's app, with settings manually transcribed by a patient user from the form to a software application on a companion device.
Figure 10:
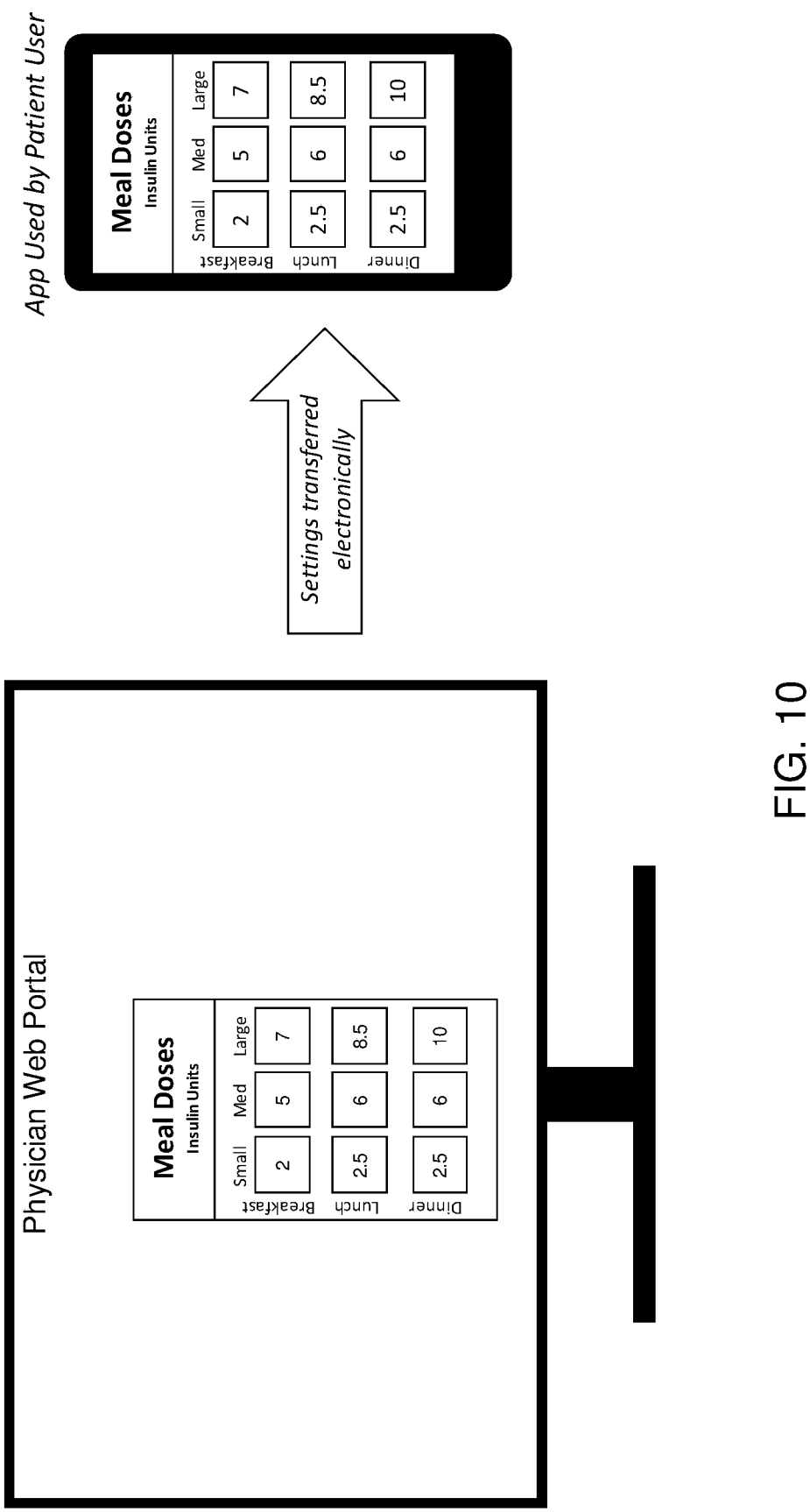
FIG. 10 shows an illustration depicting a web portal for entering user settings, with the settings electronically transferred to a software application on a companion device.
Figure 11:
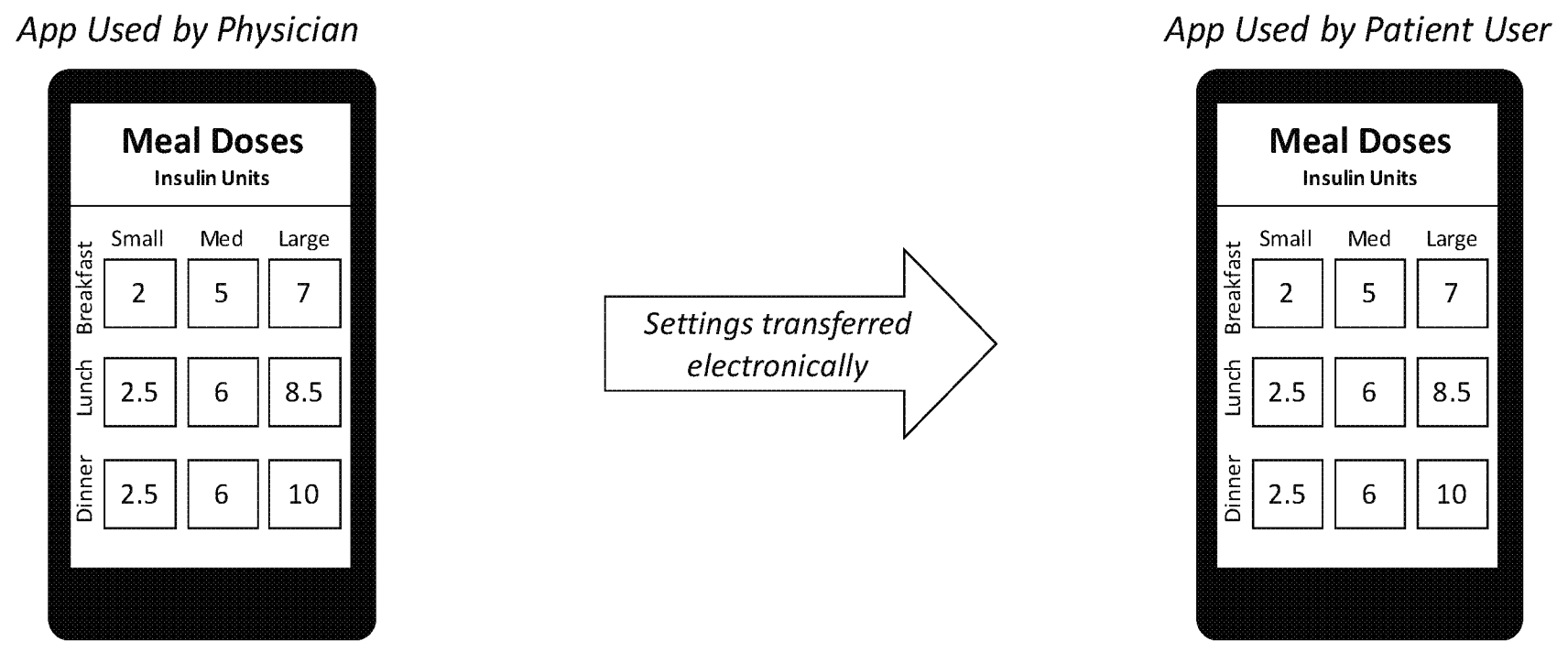

FIGS. 9-11 show illustrations depicting various examples for transferring settings of the streamlined dose calculator module 220 from a physician or other health care provider (HCP) manually or electronically, for initial setup and for ongoing adjustments of the streamlined dose calculator.

FIG. 9 shows an illustration depicting a paper prescription form with a section matching the patient user's app, with settings manually transcribed by a patient user from the form to a software application on a companion device. The paper prescription form has a section that visually correlates to the user's app. In this example implementation, the physician or HCP enters the desired settings manually onto the prescription form, and the patient user then manually transcribes these settings into the app. Not only do the settings have matching labels on the form and in the app, but the visual layout is similar to help the patient user enter the data easily and accurately. Settings for dose calculators or other dose therapy protocols are critical and can be harmful if entered incorrectly, so it is critical that the user does not make a transcription error.

FIG. 10 shows an illustration depicting a web portal for entering user settings, with the settings electronically transferred to a software application on a companion device. In this example, the web portal is used by a physician or HCP for entering user settings, which are then they securely and automatically transferred to the patient user's app via the Internet or other wireless communication.

FIG. 11 shows an illustration depicting a physician app for entering user settings, with the settings electronically transferred to a software application on a companion device. Similarly, the example of FIG. 11 shows the settings electronically transferred to the patient user's application from the physician's or HCP's app. Electronic transfer of settings may be done automatically without any action from the patient user, or with a required confirmation by the patient user before activating the new settings.

In some implementations of titration dosing mode, the system 100 can then allow selection of which type of dose regimen to use, and its applicable parameters. This could be set directly in the app via a device of the system (e.g., companion device 5), or by a physician or other HCP remotely through the cloud from a separate and connected application or web interface. For such dose regimen implementations, options may include a dose calculator (with carb input for meals), fixed dose therapy, select sliding scale, or any other method of dose selection desired by the physician.

In an example implementation of the titration dosing mode of the streamlined dose calculator module 220, the module 220 can begin by recommending a small dose (for example, 2 units) for each meal. The module 220 can then monitor the dosing behavior and analyte (e.g., glucose) response of the patient user, e.g., over two or more dosing periods, to determine how the patient user responds to the medicine (e.g., insulin) with respect to a target analyte value. For example, the streamlined dose calculator module 220, operating in the titration mode, can determine when the patient user intakes a meal (e.g., based on user input) and how the patient user's glucose levels responded to a dose administered (e.g., by the pen device 10) to lower the increased glucose levels to a target value or range. The streamlined dose calculator module 220, operating in the titration mode, can apply the determination protocol over the course of two or more meals, for example, and analyze the determined data. The streamlined dose calculator module 220, operating in the titration mode, can then gradually increase the mealtime recommendation for recommending future medicine doses based on the analyzed data. For example, if the streamlined dose calculator module 220 determines that the initial recommended dose (e.g., 2 units) is insufficient to lower the patient user's glucose level to a target value or range, then the recommended mealtime dose may be increased to 3 units. The streamlined dose calculator module 220, operating in the titration mode, can evaluate the effectiveness of such recommended doses.

An example of the titration protocol can include the following method. The example titration protocol can include (a) receiving an updated analyte value corresponding to the current analyte level; (b) determining whether the updated analyte value is within a range associated with the target analyte level; when it is determined that the updated analyte value is above the range after one or more meals, (c) re-calculating a second titration dose according to the titration protocol, and displaying the second titration dose on the display device; and repeating (a), (b), (c) until the current analyte level reaches the target analyte level acceptable well after meals.

Insulin Type Modeling Module

Modern insulins are available in multiple action times, such as "fast-acting" designed to match the response time of food (several hours), and "long-acting" designed to work slowly and cover basal (steady background) needs for approximately 24 hours. Fast-acting and long-acting insulin medicines are designed to have practical action times and steady (flat) responses in the body. However, these types of insulin can be expensive and cost-prohibitive for some people with diabetes.

The plot of insulin action over time is known as the PK/PD profile, which stands for pharmacokinetics and pharmacodynamics. Pharmacokinetics relates to the absorption and metabolism of a drug in the body, and pharmacodynamics relates to the body's response to a concentration of drug.

Older and less-expensive insulins are readily available, but they have more intermediate response times (e.g., 4-12 hours) with less consistent responses in the body. For example, older and less-expensive insulin medications may have a large immediate peak and then a sudden decay, followed by a long period of lower activity. Because of these factors, it is more difficult for patient users to manually calculate their effect on glucose levels, and it is more likely to lead to insulin stacking, which is when insulin is taken by the patient for the purposes of a glucose correction or a meal correction but a previous dose is still active in his/her body since the action time is much longer than a meal lasts.

In some implementations, the app of the companion device 5 is configured to analyze and model the behavior of various types of a medicine, such as insulin, based on the patient user's usage and response to the medicine. In some embodiments, the software architecture 200 can include a medicine type modeling module 240. In some implementations, the medicine type modeling module 240 can be tailored to work with less-expensive insulin by accurately modeling its irregular physiological response, and keep an accurate measure of insulin remaining in the body (IOB) so that an accurate dose can be calculated, e.g., by a dose calculator module that can be part of the software app on the companion device 5. The medicine type modeling module 240 implemented by the system 100 can allow the selection of the type of insulin being used, e.g., loaded in the pen device 10 for dispensing, and can continuously or intermittently calculate PK/PD that would be tailored to that type of insulin. As a result of implementations of the medicine type modeling module 240 monitoring and updating dose calculations based on the type of insulin being administered by the pen device 10, for example, less expensive insulin could be used by diabetic patients more safely and more effectively for controlling their glucose levels. For example, PK/PD profiles can also grow more accurate over time, e.g., further improving IOB accuracy, and therefore dose recommendation accuracy, when combined with BG or CGM data. For example, a patient user's own insulin response could be inferred over time by the medicine type modeling module 240 implemented by the system 100; and similarly, a population's response to a particular insulin could be aggregated and averaged, and thereby be used to refine the PD/PD profile for a particular insulin, and possibly for a particular population subgroup (e.g., based on gender, age, nationality, etc.). The response could be measured by averaging glucose response after a dose, and averaging this data over many doses, scaling for the size of the dose and any other known information, such as meals or exercise affecting the response.

Priming User Education Based on Behavior

Insulin pens benefit from being primed before each use, and generally instruct the patient user to do so in the instructions. Priming involves dispensing a small dose in the air before taking a therapeutic dose to ensure an accurate dose is correctly delivered. This clears out any air in the needle or cartridge, takes up any mechanical backlash in the system, and confirms to the user that the needle is not clogged and the device is working.

However, anecdotally, it is observed that many patient users do not prime their insulin pens, often not understanding that it is beneficial for accuracy. Instructions are often not read by the patient users, and even constant warnings reminding users to prime may go disregarded.

In implementations of the system 100, the pen device 10 can detect and distinguish dosing events and priming events, and communicate with the patient user via a user interface displayed on the companion device 5 (or pen device 10) via the app. As such, the system 100 can know explicitly whether the user is priming or not. In this case, for example, patient users who prime correctly may be undisturbed, whereas patient users who do not prime can be alerted to the need and educated in-context of their negligent behavior (i.e., non-priming). Directly after taking a dose without priming, some time period after they have dosed, or immediately before an anticipated next dose (for example, anticipated due to a regular schedule, a dose reminder or recommendation, or use of a manual dose calculator), the system 100 can provide the patient user a message about and/or a summary of the patient user's instance and/or pattern of not priming the pen device 10 before dispensing a dose. In some examples, the message and/or summary can be combined with text or video instructions or other explanation of the importance of priming. By displaying the message or summary in-context of the behavior, users would have a better chance of modifying their behavior to include priming, therefore improving the accuracy of their insulin delivery and therefore ultimately their glycemic control. An in-context message may appear after a dose is taken without priming, or may occur the next time a dose calculator is used or the app is opened, with the intent of educating the user just before their next dose. Metrics of priming could also be reported to physicians, letting them know how often the user does not prime, or alerting them to users who do and do not prime, giving the physician a chance to explain the importance and reinforce good behavior as well.

Examples

In some embodiments in accordance with the present technology (example A1), a method for autonomously determining an insulin dose includes receiving, by a software application operable on a mobile computing device of a patient user, one or more glucose values associated with a health condition of the patient user; determining, by the software application, an insulin metric value associated with the patient user based on insulin on board (IOB) data pertaining to an estimated amount of insulin medicine active in the body of the patient user; autonomously calculating, by the software application, a dose of the insulin medicine based at least on the one or more glucose values and the insulin metric value; and continuously displaying, on a display of the mobile computing device or a device in communication with the mobile computing device, the calculated dose of the insulin medicine, in which at least the determining, the calculating and the continuously displaying requires no user input action of the patient user.

Example A2 includes the method of example A1, in which the calculated dose of the insulin medicine includes a next-recommended dose of the insulin medicine including a dose amount, a type of insulin and a time of dose.

Example A3 includes the method of example A1, in which the determining the insulin metric value includes autonomously calculating the IOB data based on one or more previous doses of an insulin medication administered to the patient user, including a dose amount, a type of the insulin medication, and a time of administration of the previous dose.

Example A4 includes the method of example A1, of which the determining the insulin metric value includes receiving the one or more glucose values and confirming an authenticity of the received one or more glucose values.

Example A5 includes the method of example A1, further including receiving, by the software application, contextual data associated with the patient user obtained by the mobile computing device, of which the obtained contextual data includes information pertaining to one or more of a measured heart rate of the patient user, a measured blood pressure of the patient user, a physical activity including at least one of an activity or exercise by the patient user, a location of the patient user, or a mental state of the patient user.

Example A6 includes the method of example A1, of which the mobile computing device includes a smartphone, a tablet, a smartwatch, or an injection pen device.

Example A7 includes the method of example A1, of which the continuously displaying includes displaying the calculated dose of the insulin medicine on a home screen, on an app screen, or in a form of a notification or a widget of the mobile computing device.

Example A8 includes the method of example A1, further including generating an assumption associated with a carbohydrate metric including one or more of a carbohydrate-to-insulin ratio, or an insulin correction factor.

Example A9 includes the method of example A1, the calculated dose of the insulin medicine is associated with a current correction insulin dose to reach a target glucose level.

Example A10 includes the method of example A1, further including receiving, by the software application, contextual data associated with the patient user obtained by the mobile computing device, of which the obtained contextual data includes information associated with a meal including at least one of an amount of carbohydrates or calories associated with the meal.

In some embodiments in accordance with the present technology (example A11), a method for determining a medicine dose for administering to a patient user by an injection pen device includes receiving, by a software application operable on a mobile computing device of the patient user, one or more analyte values associated with a health condition of the patient user; receiving, by the software application, contextual data associated with the patient user obtained by the mobile computing device, of which the obtained contextual data includes information associated with a meal including at least one of an amount of carbohydrates or calories associated with the meal; determining, by the software application, a medicine metric value associated with an amount of medicine active in the body of the patient user; autonomously calculating a dose of the medicine based at least on the one or more analyte values, the medicine metric value, and the information associated with a meal; and continuously displaying, on a display of the mobile computing device or an injection pen device in communication with the mobile computing device, the calculated dose of the medicine.

Example A12 includes the method of example A11, of which the medicine includes insulin, and the medicine metric value includes insulin on board (IOB), and of which the one or more analyte values includes one or more glucose levels.

Example A13 includes the method of example A12, the calculated dose is associated with a current correction insulin dose to reach a target glucose level.

Example A14 includes the method of example A11, of which the receiving the information associated with the meal requires no user input action by the patient user to initiate or launch the software application in order to input the information.

Example A15 includes the method of example A11, of which the contextual data further includes information pertaining to one or more of a measured heart rate of the patient user, a measured blood pressure of the patient user, a physical activity including at least one of an activity or exercise by the patient user, a location of the patient user, or a mental state of the patient user.

Example A16 includes the method of example A11, of which the information associated with the meal includes a preset input indicative of a particular sized meal.

Example A17 includes the method of example A16, of which the particular sized meal includes one or more of (i) a small meal including a first predetermined amount of carbohydrates or calories, (ii) a medium meal including a second predetermined amount of carbohydrates or calories, (iii) a large meal including a third predetermined amount of carbohydrates or calories, or (iv) a snack meal including a fourth predetermined amount of carbohydrates or calories.

Example A18 includes the method of example A16, of which the particular sized meal is calculated by the software application based at least in part on a time of day, a recent meal eaten by the patient user, or historical meal information including a meal pattern.

Example A19 includes the method of example A11, including autonomously determining an amount of carbohydrates or calories for intake by the patient user; and displaying the determined amount of carbohydrates or calories.

Example A20 includes the method of example A11, including determining a subtype of the medicine to be dispensed by the injection pen device, of which different subtypes of the medicine differ in one or both of pharmacokinetics (PK) and pharmacodynamics (PD) of the medicine, in which the autonomously calculating the dose is further based on a PK-PD profile of the subtype of the medicine.

In some embodiments in accordance with the present technology (example A21), a method for determining an insulin dose includes receiving, by a software application operable on a mobile computing device of a patient user, one or more glucose values associated with a health condition of the patient user; determining, by the software application, an insulin metric value associated with the patient user based on insulin on board (IOB) data pertaining to an estimated amount of insulin medicine active in the body of the patient user; autonomously calculating, by the software application, a dose of the insulin medicine based at least on the one or more glucose values and the insulin metric value, and a pre-set fixed-dose therapy schedule developed by a health care provider of the patient user; and providing, on a display of the mobile computing device or a device in communication with the mobile computing device, a notification associated with the calculated dose of the insulin medicine and a corresponding time according to the pre-set fixed-dose therapy schedule.

Example A22 includes the method of example A21, of which at least the determining, the calculating and the providing requires no user input action of the patient user.

In some embodiments in accordance with the present technology (example A23), a method for determining an insulin dose includes receiving, by a software application operable on a mobile computing device of a patient user, one or more glucose values associated with a health condition of the patient user; determining, by the software application, an insulin metric value associated with the patient user based on insulin on board (IOB) data pertaining to an estimated amount of insulin medicine active in the body of the patient user; autonomously calculating, by the software application, a dose of the insulin medicine based at least on the one or more glucose values and the insulin metric value, of which the autonomously calculating the dose of the insulin medicine includes determining a first dose of a sequence of titration doses of the insulin medicine according to a titration protocol to cause a current glucose level of the patient user to lower a target glucose level; displaying, on a display of the mobile computing device or a device in communication with the mobile computing device, the calculated dose of the insulin medicine; and monitoring a response to administration of the first dose, including: (a) receiving an updated glucose value corresponding to the current glucose level, (b) determining whether the updated glucose value is within a range associated with the target glucose level, (c) when it is determined that the updated glucose value is above the range after one or more meals, re-calculating a second dose according to the titration protocol, and displaying the second dose on the display device, and (d) repeating (a), (b), (c) until the current glucose level reaches the target glucose level acceptable within a predetermined time frame.

Example A24 includes the method of example A23, of which at least the determining, the calculating, and the displaying requires no user input action of the patient user.

In some embodiments in accordance with the present technology (example A25), a system for administering a medicine to a patient includes an injection pen device structured to contain a medicine cartridge and include a dose setting mechanism to set a dose of a medicine stored in the medicine cartridge to be dispensed by the injection pen device, a dispensing mechanism to dispense the medicine according to the set dose, a sensor unit to detect a dispensed dose, and an electronics unit including a processor, a memory, and a wireless transmitter, the electronics unit configured to process the detected dispensed dose with time data associated with a dispensing event to generate dose data, and to wirelessly transmit the dose data; and a mobile communication device in wireless communication with the injection pen device, the mobile communication device including a data processing unit including a processor and memory to receive and process the dose data, of which at least one of the injection pen device or the mobile communication device includes a software application program product comprising a non-transitory computer-readable storage medium having instructions, which when executed by the processor, cause the device to determine a recommended dose and display the recommended dose on a display of the mobile communication device or the injection pen device.

Example A26 includes the system of example A25, of which the software application includes a data aggregator module to receive one or more of: (i) one or more analyte values associated with a health condition of the patient user, a medicine metric value associated with an amount of the medicine active in the body of the patient user, or (iii) information associated with a meal including at least one of an amount of carbohydrates or calories associated with the meal; a streamlined dose calculator module to autonomously calculate the recommended dose of the medicine based at least upon the one or more analyte values and the medicine metric value.

Example A27 includes the system of example A26, of which the one or more analyte values include glucose values and the medicine includes insulin, and of which the streamlined dose calculator module is configured to autonomously calculate the recommend dose of the insulin by: determining an insulin metric value associated with the patient user based on insulin on board (IOB) data pertaining to an estimated amount of insulin medicine active in the body of the patient user; autonomously calculating a dose of the insulin medicine based at least on the one or more glucose values and the insulin metric value; and continuously displaying, on the display, the calculated dose of the insulin medicine, of which at least the determining, the calculating and the continuously displaying requires no user input action of the patient user.

Example A28 includes the system of example A25, of which the data aggregator module is configured to receive contextual data associated with the patient user obtained by the mobile computing device, the contextual data including information pertaining to one or more of a measured heart rate of the patient user, a measured blood pressure of the patient user, a physical activity including at least one of an activity or exercise by the patient user, a location of the patient user, or a mental state of the patient user.

Example A29 includes the system of example A25, of which the mobile communication device includes a smartphone, a tablet, a wearable computing device including a smartwatch or smartglasses, a computer including a laptop computer, or one or more computers networked in a communication network through the Internet.

In some embodiments in accordance with the present technology (example B1), a system for administering a medicine includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data, the injection pen device in wireless communication with a mobile communication device including a data processing unit including a processor and memory to receive and process the dose data, in which the mobile communication device includes a software application program product comprising a non-transitory computer-readable storage medium having instructions, which when executed by the processor of the data processing unit, cause the mobile communication device to determine a recommended dose based on health data and contextual data associated with a user of the injection pen device, the health data including one or more analyte values associated with a health condition, and the contextual data including one or more of physical activity data, location data, or nutrient data corresponding to a food, in which the software application program product includes (i) a data aggregator that obtains the health data and the contextual data, (ii) a dose calculator that autonomously determines the recommended dose of the medicine, and (iii) a user interface generator to produce a user interface on a display of the mobile communication device that persistently displays, on the produced user interface, the recommended dose.

Example B2 includes the system of example B1, in which dose calculator autonomously determines the recommended dose of the medicine based on the health data and contextual data without user input action of the user on the user interface.

Example B3 includes the system of examples B1 or B2, in which the instructions, when executed by the processor of the data processing unit, cause the mobile communication device to: receive the one or more analyte values associated with the health condition to which the medicine is associated; receive the health data and the contextual data associated with the user; determine a medicine metric value associated with an amount of medicine active in the body of the user; autonomously calculate the recommended dose of the medicine without input from the user based at least on the one or more analyte values, the medicine metric value, and the contextual data including the nutrient data; and continuously display, on the display of the mobile computing device, the recommended dose of the medicine.

Example B4 includes the system of example B1, in which the user interface generator produces the user interface to display information associated with a meal that includes a preset input indicative of a particular sized meal.

Example B5 includes the system of example B4, in which the medicine includes insulin, and the one or more analyte values include one or more glucose values, and in which the particular sized meal includes one or more of (i) a small meal including a first predetermined amount of carbohydrates, (ii) a medium meal including a second predetermined amount of carbohydrates, (iii) a large meal including a third predetermined amount of carbohydrates, or (iv) a snack or dessert meal including a fourth predetermined amount of carbohydrates.

Example B6 includes the system of example B5, in which the medicine includes insulin, and the one or more analyte values include one or more glucose values, and in which the particular sized meal is determined by the software application based at least in part on a time of day, the location data, a recent meal eaten by the user, or historical meal information including a meal pattern.

Example B7 includes the system of example B1, in which the instructions, when executed by the processor of the data processing unit, cause the mobile communication device to: determine a subtype of the medicine to be dispensed by the injection pen device, in which different subtypes of the medicine differ in one or both of pharmacokinetics (PK) and pharmacodynamics (PD) of the medicine, in which the PK-PD profile of the subtype of the medicine is a calculation factor in determination of the recommended dose.

Example B8 includes the system of example B1, in which the recommended dose of the medicine is displayed as a next-recommended dose of the medicine including a dose amount, a type of medicine, and a time for dispensing the next-recommended dose.

Example B9 includes the system of example B1, in which the instructions, when executed by the processor of the data processing unit, cause the mobile communication device to display the recommended dose of the medicine on a home screen, on an application screen, or in a form of a notification or a widget of the mobile computing device.

Example B10 includes the system of example B1, in which the one or more analyte values include one or more glucose values, and the medicine includes insulin, and in which the instructions, when executed by the processor of the data processing unit, cause the mobile communication device to autonomously calculate the recommend dose of the insulin without input from the user by determining an insulin metric value associated with the patient user based on insulin on board IOB data pertaining to an estimated amount of insulin medicine active in the body of the patient user; autonomously calculating a dose of the insulin medicine based at least on the one or more glucose values and the insulin metric value; and continuously displaying, on the display, the calculated dose of the insulin medicine.

Example B11 includes the system of example B1, in which the one or more analyte values include one or more glucose values, and the medicine includes insulin, and in which the recommended dose is associated with a current correction insulin dose to reach a target glucose level.

Example B12 includes the system of example B1, in which the received one or more analyte values and/or the received health data and contextual data are imported from another software application operable on the mobile communication device.

Example B213 includes the system of example B1, in which the health data includes information pertaining to one or more of a previous dose of the medicine or a dose of another medicine taken by the user.

Example B14 includes the system of example B1, in which the contextual data further includes information pertaining to one or more of a measured heart rate of the user, a measured blood pressure of the user, an event attended or to be attended by the user, or a mental state of the user.

Example B15 includes the system of example B1, in which the mobile communication device is implemented on a smartphone, a tablet, or a wearable computing device including a smartwatch or smartglasses.

In some embodiments in accordance with the present technology (example B16), a method for determining a medicine dose for administering to a patient user by an injection pen device includes receiving, by a software application operable on a mobile computing device of the patient user, one or more analyte values associated with a health condition of the patient user; receiving, by the software application, contextual data associated with the patient user obtained by the mobile computing device, in which the obtained contextual data includes information associated with a meal including at least one of an amount of carbohydrates or calories associated with the meal; determining, by the software application, a medicine metric value associated with an amount of medicine active in the body of the patient user; autonomously calculating a dose of the medicine without input from the user based at least on the one or more analyte values, the medicine metric value, and the information associated with a meal; and continuously displaying, on a display of the mobile computing device or an injection pen device in communication with the mobile computing device, the calculated dose of the medicine.

Example B17 includes the method of example B16, in which the medicine includes insulin, and the medicine metric value includes insulin on board IOB, and in which the one or more analyte values includes one or more glucose levels.

Example B18 includes the method of example B17, in which the calculated dose is associated with a current correction insulin dose to reach a target glucose level.

Example B19 includes the method of example B16, in which the receiving the information associated with the meal requires no user input action by the patient user to initiate or launch the software application in order to input the information.

Example B20 includes the method of example B16, in which the contextual data further includes information pertaining to one or more of a measured heart rate of the patient user, a measured blood pressure of the patient user, a physical activity including at least one of an activity or exercise by the patient user, a location of the patient user, or a mental state of the patient user.

Example B21 includes the method of example B16, in which the information associated with the meal includes a preset input indicative of a particular sized meal.

Example B22 includes the method of example B21, in which the particular sized meal includes one or more of (i) a small meal including a first predetermined amount of carbohydrates or calories, (ii) a medium meal including a second predetermined amount of carbohydrates or calories, (iii) a large meal including a third predetermined amount of carbohydrates or calories, or (iv) a snack meal including a fourth predetermined amount of carbohydrates or calories.

Example B23 includes the method of example B21, in which the particular sized meal is calculated by the software application based at least in part on a time of day, a recent meal eaten by the patient user, or historical meal information including a meal pattern.

Example B24 includes the method of example B16, including autonomously determining an amount of carbohydrates or calories for intake by the patient user; and displaying the determined amount of carbohydrates or calories.

Example B25 includes the method of example B16, including determining a subtype of the medicine to be dispensed by the injection pen device, in which different subtypes of the medicine differ in one or both of pharmacokinetics (PK) and pharmacodynamics (PD) of the medicine, in which the autonomously calculating the dose is further based on a PK-PD profile of the subtype of the medicine.

Example B26 includes the method of example B16, in which the method is implemented on a smartphone, a tablet, a medicine injection pen, a medicine injection pump, or a wearable computing device including a smartwatch or smartglasses.

In some embodiments in accordance with the present technology (example B27), a method for autonomously adjusting a predetermined fixed insulin dose, includes receiving, by a software application operable on a mobile computing device of a patient user, one or more glucose values associated with a health condition of the patient user; determining, by the software application, an insulin metric value associated with the patient user based on insulin on board (IOB) data pertaining to an estimated amount of insulin medicine active in the body of the patient user; autonomously calculating, by the software application, a dose of the insulin medicine without input from the user based at least on the one or more glucose values and the insulin metric value, in which the autonomously calculating the dose of the insulin medicine includes determining a first dose of a sequence of titration doses of the insulin medicine according to a titration protocol to cause a current glucose level of the patient user to lower a target glucose level; displaying, on a display of the mobile computing device or a device in communication with the mobile computing device, the calculated dose of the insulin medicine; and monitoring a response to administration of the first dose, including: (a) receiving an updated glucose value corresponding to the current glucose level, (b) determining whether the updated glucose value is within a range associated with the target glucose level, (c) when it is determined that the updated glucose value is above the range after one or more meals, re-calculating a second dose according to the titration protocol, and displaying the second dose on the display device, and (d) repeating (a), (b), (c) until the current glucose level reaches the target glucose level acceptable within a predetermined time frame.

Example B28 includes the method of example B26, in which at least the determining, the calculating, and the displaying requires no user input action of the patient user.

Example B29 includes the method of example B27, in which the method is implemented on a smartphone, a tablet, a medicine injection pen, a medicine injection pump, or a wearable computing device including a smartwatch or smartglasses.

In some embodiments in accordance with the present technology (example B30), a system for administering a medicine includes an injection pen device including a dose setting mechanism to set a dose of a medicine contained in a medicine cartridge that is to be dispensed by the injection pen device, a dispensing mechanism to dispense the medicine according to the set dose, a display screen to display information, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data, the injection pen device including a software application program product comprising a non-transitory computer-readable storage medium having instructions, which when executed by the processor of the injection pen device, cause the injection pen device to determine a recommended dose based on health data and contextual data associated with a user of the injection pen device, the health data including one or more analyte values associated with a health condition, and the contextual data including one or more of physical activity data, location data, or nutrient data corresponding to a food, in which the software application program product includes (i) a data aggregator that obtains the health data and the contextual data, (ii) a dose calculator that autonomously determines the recommended dose of the medicine, and (iii) a user interface generator to produce a user interface on the display screen that persistently displays, on the produced user interface, the recommended dose.

Example B31 includes the system of example B30, in which dose calculator autonomously determines the recommended dose of the medicine based on the health data and contextual data without user input action of the user on the user interface.

Example B32 includes the system of examples B30 or B31, in which the instructions, when executed by the processor of the data processing unit, cause the injection pen device to: receive the one or more analyte values associated with the health condition to which the medicine is associated; receive the health data and the contextual data associated with the user; determine a medicine metric value associated with an amount of medicine active in the body of the user; autonomously calculate the recommended dose of the medicine without input from the user based at least on the one or more analyte values, the medicine metric value, and the contextual data including the nutrient data; and continuously display, on the display of the injection pen device, the recommended dose of the medicine.

Example B33 includes the system of example B30, in which the user interface generator produces the user interface to display information associated with a meal that includes a preset input indicative of a particular sized meal.

Example B34 includes the system of example B33, in which the medicine includes insulin, and the one or more analyte values include one or more glucose values, and in which the particular sized meal includes one or more of (i) a small meal including a first predetermined amount of carbohydrates, (ii) a medium meal including a second predetermined amount of carbohydrates, (iii) a large meal including a third predetermined amount of carbohydrates, or (iv) a snack or dessert meal including a fourth predetermined amount of carbohydrates.

Example B35 includes the system of example B33, in which the medicine includes insulin, and the one or more analyte values include one or more glucose values, and in which the particular sized meal is determined by the software application based at least in part on a time of day, the location data, a recent meal eaten by the user, or historical meal information including a meal pattern.

In some embodiments in accordance with the present technology (example B36), a method for determining an insulin dose for administering to a patient user by an medicine injection device includes receiving, by a software application operable on the medicine injection device or a mobile computing device of the patient user in communication with the medicine injection device, one or more glucose values associated with a health condition of the patient user; receiving, by the software application, contextual data associated with the patient user obtained by the mobile computing device, in which the obtained contextual data includes information associated with a meal including at least one of an amount of carbohydrates associated with the meal; determining, by the software application, an insulin on board (IOB) metric value associated with an amount of insulin active in the body of the patient user; autonomously calculating a dose of the insulin without input from the user based at least on the one or more glucose values, the IOB metric value, and the information associated with a meal; and continuously displaying, on a display of the mobile computing device or the medicine injection device, the calculated dose of the insulin, in which the calculated dose is associated with a current correction insulin dose to reach a target glucose level.

Example B37 includes the method of example B36, in which the calculated dose is determined to be a predetermined fixed size based on a particular sized meal or type of meal, or a combination thereof.

Example B38 includes the method of example B36, in which the information associated with the meal includes a preset input indicative of a particular sized meal or type of meal, or combination thereof.

Example B39 includes the method of example B38, in which the particular sized meal includes one or more of (i) a small meal including a first predetermined amount of carbohydrates or calories, (ii) a medium meal including a second predetermined amount of carbohydrates or calories, (iii) a large meal including a third predetermined amount of carbohydrates or calories, or (iv) a snack meal including a fourth predetermined amount of carbohydrates or calories.

Example B40 includes the method of example B38, in which the particular sized meal is calculated by the software application based at least in part on a time of day, a recent meal eaten by the patient user, or historical meal information including a meal pattern.

Example B41 includes the method of example B36, wherein the method is implemented on a smartphone, a tablet, a medicine injection pen, a medicine injection pump, or a wearable computing device including a smartwatch or smartglasses.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for administering a medicine, comprising:
an injection pen device including a dose setting mechanism to set a dose of a medicine contained in a medicine cartridge that is to be dispensed by the injection pen device, a dispensing mechanism to dispense the medicine according to the set dose, a processor, a memory including instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data;
the injection pen device in wireless communication with a mobile communication device that includes a data processing unit including a processor and memory to receive and process the dose data; and
a sensor device configured to be coupled to a patient for determining an analyte value associated with a health condition of the patient, the sensor device in wireless communication with the mobile communication device for communicating, in real-time, the analyte value determined by the sensor device to the mobile communication device,
wherein the mobile communication device includes a software application comprising a non-transitory computer-readable storage medium having instructions, which when executed by the processor of the data processing unit, cause the mobile communication device to determine a recommended dose of the medicine based on the analyte value communicated from the sensor device and contextual data associated with a user of the injection pen device, the contextual data including one or more of physical activity data, location data, or nutrient data corresponding to a food, wherein the software application includes:
(i) a data aggregator that obtains the analyte value and the contextual data,
(ii) a dose calculator that autonomously determines, without user input, the recommended dose of the medicine based on the analyte value and the contextual data obtained by the data aggregator, and
(iii) a user interface generator to produce a user interface on a display of the mobile communication device that persistently and dynamically displays, on the produced user interface, the recommended dose of the medicine autonomously determined by the dose calculator.

2. The system of claim 1, wherein the dose calculator autonomously determines the recommended dose of the medicine based on the analyte value and the contextual data without user input action of the user on the user interface.

3. The system of claim 1, wherein the instructions, when executed by the processor of the data processing unit, cause the mobile communication device to:
receive the analyte value to which the health condition is associated;
receive the analyte value and the contextual data associated with the user;
determine a medicine metric value associated with an amount of medicine active in the body of the user;
autonomously calculate the recommended dose of the medicine via the dose calculator without input from the user based at least on the analyte value, the medicine metric value, and the contextual data; and
continuously display, on the display of the mobile computing device, the recommended dose of the medicine.

4. The system of claim 1, wherein the user interface generator produces the user interface to display information associated with a meal that includes a preset input indicative of a particular sized meal.

5. The system of claim 4, wherein the medicine includes insulin, and the analyte value includes one or more glucose values, and wherein the particular sized meal includes one or more of (i) a small meal including a first predetermined amount of carbohydrates, (ii) a medium meal including a second predetermined amount of carbohydrates, (iii) a large meal including a third predetermined amount of carbohydrates, or (iv) a snack or dessert meal including a fourth predetermined amount of carbohydrates.

6. The system of claim 5, wherein the medicine includes insulin, and the analyte value includes one or more glucose values, and wherein the particular sized meal is determined by the software application based at least in part on a time of day, the location data, a recent meal eaten by the user, or historical meal information including a meal pattern.

7. The system of claim 1, wherein the instructions, when executed by the processor of the data processing unit, cause the mobile communication device to:
determine a subtype of the medicine to be dispensed by the injection pen device,
wherein different subtypes of the medicine differ in one or both of pharmacokinetics (PK) and pharmacodynamics (PD) of the medicine,
wherein the PK-PD profile of the subtype of the medicine is a calculation factor in determination of the recommended dose.

8. The system of claim 1, wherein the recommended dose of the medicine is displayed as a next-recommended dose of the medicine including a dose amount, a type of medicine, and a time for dispensing the next-recommended dose.

9. The system of claim 1, wherein the instructions, when executed by the processor of the data processing unit, cause the mobile communication device to display the recommended dose of the medicine on a home screen, on an application screen, or in a form of a notification or a widget of the mobile computing device.

10. The system of claim 1, wherein the analyte value includes one or more glucose values, and the medicine includes insulin, and wherein the instructions, when executed by the processor of the data processing unit, cause the mobile communication device to:

autonomously calculate the recommend dose of the insulin via the dose calculator without input from the user by determining an insulin metric value associated with the patient user based on insulin on board (IOB) data pertaining to an estimated amount of insulin medicine active in the body of the patient user;
   autonomously calculate a dose of the insulin medicine via the dose calculator based at least on the one or more glucose values and the insulin metric value; and
   continuously display, on the display, the calculated dose of the insulin medicine.

11. The system of claim 1, wherein the analyte value includes one or more glucose values, and the medicine includes insulin, and wherein the recommended dose is associated with a current correction insulin dose to reach a target glucose level.

12. The system of claim 1, wherein at least one of the analyte value or the contextual data is imported from another software application operable on the mobile communication device.

13. The system of claim 1, wherein the instructions, when executed by the processor of the data processing unit, cause the mobile communication device to:

determine the recommended dose of the medicine further based on information pertaining to one or more of a previous dose of the medicine or a dose of another medicine taken by the user.

14. The system of claim 1, wherein the contextual data further includes information pertaining to one or more of a measured heart rate of the user, a measured blood pressure of the user, an event attended or to be attended by the user, or a mental state of the user.

15. The system of claim 1, wherein the mobile communication device is implemented on a smartphone, a tablet, or a wearable computing device including a smartwatch or smartglasses.

16. A method for determining a medicine dose for administering to a patient user by an injection pen device, comprising:

receiving, by a software application operable on a mobile computing device of the patient user, one or more analyte values from a sensor device configured to be coupled to the patient user for determining the one or more analyte values;
   receiving, by the software application, information associated with a meal including at least one of an amount of carbohydrates or calories associated with the meal;
   determining, by the software application, a medicine metric value associated with an amount of medicine active in the body of the patient user;
   autonomously calculating a dose of a medicine to be dispensed by the injection pen device without input from the user based at least on the one or more analyte values received from the sensor device, the medicine metric value, and the information associated with the meal; and
   continuously and dynamically displaying, on a display of the mobile computing device or an injection pen device in communication with the mobile computing device, the autonomously calculated dose of the medicine.

17. The method of claim 16, wherein the medicine includes insulin, and the medicine metric value includes insulin on board (IOB), and wherein the one or more analyte values includes one or more glucose levels.

18. The method of claim 17, wherein the calculated dose of the medicine is associated with a current correction insulin dose to reach a target glucose level.

19. The method of claim 16, wherein receiving the information associated with the meal requires no user input action by the patient user to initiate or launch the software application in order to input the information.

20. The method of claim 16, further comprising receiving, by the software application, information pertaining to one or more of a measured heart rate of the patient user, a measured blood pressure of the patient user, a physical activity including at least one of an activity or exercise by the patient user, a location of the patient user, or a mental state of the patient user.

21. The method of claim 16, wherein the information associated with the meal includes a preset input indicative of a particular sized meal.

22. The method of claim 21, wherein the particular sized meal includes one or more of (i) a small meal including a first predetermined amount of carbohydrates or calories, (ii) a medium meal including a second predetermined amount of carbohydrates or calories, (iii) a large meal including a third predetermined amount of carbohydrates or calories, or (iv) a snack meal including a fourth predetermined amount of carbohydrates or calories.

23. The method of claim 21, wherein the particular sized meal is calculated by the software application based at least in part on a time of day, a recent meal eaten by the patient user, or historical meal information including a meal pattern.

24. The method of claim 16, further comprising:
   autonomously determining an amount of carbohydrates or calories for intake by the patient user; and
   displaying the determined amount of carbohydrates or calories.

25. The method of claim 16, comprising:
   determining a subtype of the medicine to be dispensed by the injection pen device, wherein different subtypes of the medicine differ in one or both of pharmacokinetics (PK) and pharmacodynamics (PD) of the medicine,
   wherein the autonomously calculating the dose of the medicine is further based on a PK-PD profile of the subtype of the medicine.

26. The method of claim 16, wherein the method is implemented on a smartphone, a tablet, a medicine injection pen, a medicine injection pump, or a wearable computing device including a smartwatch or smartglasses.

* * * * *